US006156517A

United States Patent [19]

Mayfield

[11] Patent Number: 6,156,517

[45] Date of Patent: Dec. 5, 2000

[54] RNA BINDING PROTEIN AND BINDING SITE USEFUL FOR EXPRESSION OF RECOMBINANT MOLECULES

[75] Inventor: Stephen Mayfield, Cardiff, Calif.

[73] Assignee: The Scripps Research Institute, La Jolla, Calif.

[21] Appl. No.: 09/341,550

[22] PCT Filed: Jan. 16, 1998

[86] PCT No.: PCT/US98/00840

§ 371 Date: Jul. 13, 1999

§ 102(e) Date: Jul. 13, 1999

[87] PCT Pub. No.: WO98/31823

PCT Pub. Date: Jul. 23, 1998

Related U.S. Application Data

[60] Provisional application No. 60/035,955, Jan. 17, 1997, and provisional application No. 60/069,400, Dec. 12, 1997.

[51] Int. Cl.$^{7}$ ........................ C12Q 1/68

[52] U.S. Cl. ........................ 435/6; 435/320.1; 435/419; 435/69.1; 435/375; 435/468; 536/23.1

[58] Field of Search ........................ 435/6, 320.1, 419, 435/69.1, 375, 468; 536/23.1

[56] References Cited

PUBLICATIONS

Danon et al., *EMBO J.*, vol. 10, 1991, pp. 3993–4001.

Danon et al., *EMBO J.*, vol. 13, 1994, pp. 2227–2235.

*Primary Examiner*—James Ketter

*Attorney, Agent, or Firm*—Thomas Fitting; Emily Holmes

[57] ABSTRACT

The present invention relates to a gene expression system in eukaryotic and prokaryotic cells, preferably plant cells and intact plants. In particular, the invention relates to an expression system having a RB47 binding site upstream of a translation initiation site for regulation of translation mediated by binding of RB47 protein, a member of the poly(A) binding protein family. Regulation is further effected by RB60, a protein disulfide isomerase. The expression system is capable of functioning in the nuclear/cytoplasm of cells and in the chloroplast of plants. Translation regulation of a desired molecule is enhanced approximately 100 fold over that obtained without RB47 binding site activation.

63 Claims, 17 Drawing Sheets

```
  1 GAATTCGCGGCCGCTCCGTGGTTGGTCCTC ATG GTG TCT TTT TGA AGAGGACCTGAGCCTTTCACCCAAATATA 74
  1                                M   V   S   F   *                                5

 75 TCAAAAAACCCGGGCAACCGGCCAAAAAAATTGCAAAAGCCTCTCGTAGGCACAAAAGACCTATTCTAGCCATCAACTTT 154

155 GTATCCGACGCTGCCGTTTAGCTGCGCGTCTTGAAGTCAAGC ATG GCG ACT ACT GAG TCC TCG GCC CCG   223
  1                                            M   A   T   T   E   S   S   A   P     9

224 GCG GCC ACC ACC CAG CCG GCC AGC ACC CCG CTG GCG AAC TCG TCG CTG TAC GTC GGT GAC 283
 10 A   A   T   T   Q   P   A   S   T   P   L   A   N   S   S   L   Y   V   G   D    29

284 CTG GAG AAG GAT GTC ACC GAG GCC CAG CTG TTC GAG CTC TTC TCC TCG GTT GGC CCT GTG 343
 30 L   E   K   D   V   T   E   A   Q   L   F   E   L   F   S   S   V   G   P   V    49

344 GCC TCC ATT CGC GTG TGC CGC GAT GCC GTC ACG CGC CGC TCG CTG GGC TAC GCC TAC GTC 403
 50 A   S   I   R   V   C   R   D   A   V   T   R   R   S   L   G   Y   A   Y   V    69

404 AAC TAC AAC AGC GCT CTG GAC CCC CAG GCT GCT GAC CGC GCC ATG GAG ACC CTG AAC TAC 463
 70 N   Y   N   S   A   L   D   P   Q   A   A   D   R   A   M   E   T   L   N   Y    89

464 CAT GTC GTG AAC GGC AAG CCT ATG CGC ATC ATG TGG TCG CAC CGC GAC CCT TCG GCC CGC 523
 90 H   V   V   N   G   K   P   M   R   I   M   W   S   H   R   D   P   S   A   R   109

524 AAG TCG GGC GTC GGC AAC ATC TTC ATC AAG AAC CTG GAC AAG ACC ATC GAC GCC AAG GCC 583
110 K   S   G   V   G   N   I   F   I   K   N   L   D   K   T   I   D   A   K   A   129

584 CTG CAC GAC ACC TTC TCG GCC TTC GGC AAG ATT CTG TCC TGC AAG GTT GCC ACT GAC GCC 643
130 L   H   D   T   F   S   A   F   G   K   I   L   S   C   K   V   A   T   D   A   149

644 AAC GGC GTG TCG AAG GGC TAC GGC TTC GTG CAC TTC GAG GAC CAG GCC GCT GCC GAT CGC 703
150 N   G   V   S   K   G   Y   G   F   V   H   F   E   D   Q   A   A   A   D   R   169

704 GCC ATT CAG ACC GTC AAC CAG AAG AAG ATT GAG GGC AAG ATC GTG TAC GTG GCC CCC TTC 763
170 A   I   Q   T   V   N   Q   K   K   I   E   G   K   I   V   Y   V   A   P   F   189
```

FIG. 1A

```
764  CAG AAG CGC GCT GAC CGC CCC AGG GCA AGG ACG TTG TAC ACC AAC GTG TTC GTC AAG AAC  823
190  Q   K   R   A   D   R   P   R   A   R   T   L   Y   T   N   V   F   V   K   N    209

824  TTG CCG GCC GAC ATC GGC GAC GAC GAG CTG GGC AAG ATG GCC ACC GAG CAC GGC GAG ATC  883
210  L   P   A   D   I   G   D   D   E   L   G   K   M   A   T   E   H   G   E   I    229

884  ACC AGC GCG GTG GTC ATG AAG GAC GAC AAG GGC GGC AGC AAG GGC TTC GGC TTC ATC AAC  943
230  T   S   A   V   V   M   K   D   D   K   G   G   S   K   G   F   G   F   I   N    249

944  TTC AAG GAC GCC GAG TCG GCG GCC AAG TGC GTG GAG TAC CTG AAC GAG CGC GAG ATG AGC  1003
250  F   K   D   A   E   S   A   A   K   C   V   E   Y   L   N   E   R   E   M   S    269

1004 GGC AAG ACC CTG TAC GCC GGC CGC GCC CAG AAG AAG ACC GAG CGC GAG GCG ATG CTG CGC  1063
270  G   K   T   L   Y   A   G   R   A   Q   K   K   T   E   R   E   A   M   L   R    289

1064 CAG AAG GCC GAG GAG AGC AAG CAG GAG CGT TAC CTG AAG TAC CAG AGC ATG AAC CTG TAC  1123
290  Q   K   A   E   E   S   K   Q   E   R   Y   L   K   Y   Q   S   M   N   L   Y    309

1124 GTC AAG AAC CTG TCC GAC GAG GAG GTC GAC GAC GAC GCC CTG CGT GAG CTG TTC GCC AAC  1183
310  V   K   N   L   S   D   E   E   V   D   D   D   A   L   R   E   L   F   A   N    329

1184 TCT GGC ACC ATC ACC TCG TGC AAG GTC ATG AAG GAC GGC AGC GGC AAG TCC AAG GGC TTC  1243
330  S   G   T   I   T   S   C   K   V   M   K   D   G   S   G   K   S   K   G   F    349

1244 GGC TTC GTG TGC TTC ACC AGC CAC GAC GAG GCC ACC CGG CCG CCC GTG ACC GAG ATG AAC  1303
350  G   F   V   C   F   T   S   H   D   E   A   T   R   P   P   V   T   E   M   N    369

1304 GGC AAG ATG GTC AAG GGC AAG CCC CTG TAC GTG GCC CTG GCG CAG CGC AAG GAC GTG CGC  1363
370  G   K   M   V   K   G   K   P   L   Y   V   A   L   A   Q   R   K   D   V   R    389

1364 CGT GCC ACC CAG CTG GAG GCC AAC ATG CAG GCG CGC ATG GGC ATG GGC GCC ATG AGC CGC  1423
390  R   A   T   Q   L   E   A   N   M   Q   A   R   M   G   M   G   A   M   S   R    409
```

FIG. 1B

```
1424 CCG CCG AAC CCG ATG GCC GGC ATG AGC CCC TAC CCC GGC GCC ATG CCG TTC TTC GCT CCC  1483
 410 P   P   N   P   M   A   G   M   S   P   Y   P   G   A   M   P   F   F   A   P    429

1484 GGC CCC GGC GGC ATG GCT GCT GGC CCG CGC GCT CCG GGC ATG ATG TAC CCG CCC ATG ATG  1543
 430 G   P   G   G   M   A   A   G   P   R   A   P   G   M   M   Y   P   P   M   M    449

1544 CCG CCG CGC GGC ATG CCT GGC CCC GGC CGC GGC CCC CGC GGC CCC ATG ATG CCG CCC CAG  1603
 450 P   P   R   G   M   P   G   P   G   R   G   P   R   G   P   M   M   P   P   Q    469

1604 ATG ATG GGT GGC CCC ATG ATG GGC CCG CCC ATG GGC CCC GGG CGC GGC CGT GGC GGC CGC  1663
 470 M   M   G   G   P   M   M   G   P   P   M   G   P   G   R   G   R   G   G   R    489

1664 GGC CCC TCC GGC CGC GGC CAG GGC CGC GGC AAC AAC GCC CCT GCC CAG CAG CCC AAG CCC  1723
 490 G   P   S   G   R   G   Q   G   R   G   N   N   A   P   A   Q   Q   P   K   P    509

1724 GCC GCT GAG CCG GCC GCC GCG CCC GCC GCC GCC GCC CCC GCT GCC GCG GCG CCT GCC GCC  1783
 510 A   A   E   P   A   A   A   P   A   A   A   A   P   A   A   A   A   P   A   A    529

1784 GCG GCG GAG CCG GAG GCC CCC GCC GCC CAG CAG CCG CTG ACC GCC TCC GCG CTG GCC GCC  1843
 530 A   A   E   P   E   A   P   A   A   Q   Q   P   L   T   A   S   A   L   A   A    549

1844 GCC GCG CCG GAG CAG CAG AAG ATG ATG ATC GGC GAG CGC CTG TAC CCG CAG GTG GCG GAG  1903
 550 A   A   P   E   Q   Q   K   M   M   I   G   E   R   L   Y   P   Q   V   A   E    569

1904 CTG CAG CCC GAC CTG GCT GGC AAG ATC ACC GGC ATG CTG CTG GAG ATG GAC AAC GCC GAG  1963
 570 L   Q   P   D   L   A   G   K   I   T   G   M   L   L   E   M   D   N   A   E    589

1964 CTT CTG ATG CTT CTG GAG TCG CAC GAG GCG CTG GTG TCC AAG GTG GAC GAG GCC ATC GCT  2023
 590 L   L   M   L   L   E   S   H   E   A   L   V   S   K   V   D   E   A   I   A    609

2024 GTG CTC AAG CAG CAC AAC GTG ATT GCC GAG GAG AAC AAG GCT TAA AGCGCCTGCACGCTTGTGCG 2088
 610 V   L   K   Q   H   N   V   I   A   E   E   N   K   A   *                        624
```

FIG. 1C

```
2089 GGCTGGTGGCGCCGGCGCGCGCCGGCGCTGCTTGGGCCGCCGGCAGC ATG GGC GCG GCG GAC GCG GTG TGG 2159
   1                                                M   G   A   A   D   A   V   W   8

2160 GAG CAG TGC TTG CTG CTT CTG GCC GCC GTG AAG CCG CGC CGA ACT GGG GCG GAC GGC AGG 2219
   9 E   Q   C   L   L   L   L   A   A   V   K   P   R   R   T   G   A   D   G   R   28

2220 CTG GCG TTG ACG CCG GCG CGC CAC AAC ACA AAG TTG GTG GCG TGA AAGTCTCTGGGCGTGCTCCG 2284
  29 L   A   L   T   P   A   R   H   N   T   K   L   V   A   *                        43

2285 GACGGTTGTAAGGTTTTAAGAACTGGCTTTTGGCCGGGTTGCCGCCCAAAGGCGGAACGGCGGTCTTTTCAGGCCAATCA 2364

2365 CATCCGGCTGGAAAAATTCTTACCAAAGCCAACCCCTGCACCCAAAAATTTCGGGTTCCGAAAGAACACTCCCCTTTTTT 2444

2445 CCGGCAACGCGTTCTTTCAAGGCCAATCACTTTCCGGGTTGGAAGAAA ATG TTA CCC GGA AAA GGC GGG AAG 2516
   1                                                 M   L   P   G   K   G   G   K   8

2517 CCC CCT GCA CCC GGA CAA GTT ATT CGG GGT TTC GCC GGG AAT GAG CAA GCG TTC GGG CTG 2576
   9 P   P   A   P   G   Q   V   I   R   G   F   A   G   N   E   Q   A   F   G   L   28

2577 TTG GCC GTA TCG CGA ACG CTG TCG GGG TGT CAG GCG CCA GAA GGA AGG ATG ACG TTT TGG 2636
  29 L   A   V   S   R   T   L   S   G   C   Q   A   P   E   G   R   M   T   F   W   48

2637 TGA AGGGGTGCAAACTGAGCACACGAGTTTTGGCAATAGACGTGGAGAAAGTCCAGTGCGGGGTGAGGCGGATAGCGGA 2715
  49 *                                                                               49

2716 ATCAAGCGTGGCGGGTCCCTGGCGAGACGAGACGCTTCTGTTGTTTTGCTGAGCCCTTTG ATG GCA CAA TCG CAC 2790
   1                                                             M   A   Q   S   H   5

2791 TGT TTT GAG CAG GCG ACT GTA AAG TGC CCG ACG CTA AAA AAG CGG CCG CGA ATT CC 2846
   6 C   F   E   Q   A   T   V   K   C   P   T   L   K   K   R   P   R   I      23
```

FIG. 1D

MNRWNLLALTLGLLLVAAPFTKHQFAHASDEYEDDEEDDAPAAP

KDDDVDVTVVTVKNWDETVKKSKFALVEFYAPWCGHCKTLKPEYAKAATALKAAAPDA

LIAKVDATQEESLAQKFGVQGYPTLKWFVDGELASDYNGPRDADGIVGWVKKKTGPPA

VTVEDADKLKSLEADAEVVVVGYFKALEGEIYDTFKSYAAKTEDVVFVQTTSADVAKA

AGLDAVDTVSVVKNFAGEDRATAVLATDIDTDSLTAFVKSEKMPPTIEFNQKNSDKIF

NSGINKQLILWTTADDLKADAEIMTVFREASKKFKGQLVFVTVNNEGDGADPVTNFFG

LKGATSPVLLGFFMEKNKKFRMEGEFTADNVAKFAESVVDGTAQAVLKSEAIPEDPYE

DGVYKIVGKTVESVVLDETKDVLLEVYAPWCGHCKKLEPIYKKLAKRFKKVDSVIIAK

MDGTENEHPEIEVKGFPTILFYPAGSDRTPIVFEGGDRSLKSLTKFIKTNAKIPYELP
KKGSDGDEGTSDDKDKPASDKDEL

```
  1 gagtacgttt acgccatgaa ccgttggaac cttcttgccc ttaccctggg gctgctgctg
 61 gtggcagcgc ccttcaccaa gcaccagttt gctcatgctt ccgatgagta tgaggacgac
121 gaggaggacg atgcccccgc cgcccctaag gacgacgacg tcgacgttac tgtggtgacc
181 gtcaagaact gggatgagac cgtcaagaag tccaagttcg cgcttgtgga gttctacgct
241 ccttggtgcg gccactgcaa gaccctcaag cctgagtacg ctaaggctgc caccgccctg
301 aaggctgctg ctcccgatgc ccttatcgcc aaggtcgacg ccacccagga ggagtccctg
361 gcccagaagt tcggcgtgca gggctacccc accctcaagt ggttcgttga tggcgagctg
421 gcttctgact acaacggccc ccgcgacgct gatggcattg ttggctgggt gaagaagaag
481 actggccccc ccgccgtgac cgttgaggac gccgacaagc tgaagtccct ggaggcggac
541 gctgaggtcg ttgtcgtcgg ctacttcaag gccctggagg gcgagatcta cgacaccttc
601 aagtcctacg ccgccaagac cgaggacgtg gtgttcgtgc agaccaccag cgccgacgtc
```

FIG. 2A

```
 661 gccaaggccg ccggcctgga cgccgtggac accgtgtccg tggtcaagaa cttcgccggt
 721 gaggaccgcg ccaccgccgt cctggccacg gacatcgaca ctgactccct gaccgcgttc
 781 gtcaagtcgg agaagatgcc ccccaccatt gagttcaacc agaagaactc tgacaagatc
 841 ttcaacagcg gcatcaacaa gcagctgatt ctgtggacca ccgccgacga cctgaaggcc
 901 gacgccgaga tcatgactgt gttccgcgag gccagcaaga agttcaaggg ccagctggtg
 961 ttcgtgaccg tcaacaacga gggcgacggc gccgaccccg tcaccaactt cttcggcctc
1021 aagggcgcca cctcgcctgt gctgctgggc ttcttcatgg agaagaacaa gaagttccgc
1081 atggagggcg agttcacggc tgacaacgtg gctaagttcg ccgagagcgt ggtggacggc
1141 accgcgcagg ccgtgctcaa gtcggaggcc atccccgagg accccctatga ggatggcgtc
1201 tacaagattg tgggcaagac cgtggagtct gtggttctgg acgagaccaa ggacgtgctg
1261 ctggaggtgt acgccccctg gtgcggccac tgcaagaagc tggagcccat ctacaagaag
1321 ctggccaagc gctttaagaa ggtggattcc gtcatcatcg ccaagatgga tggcactgag
1381 aacgagcacc ccgagatcga ggtcaagggc ttccctacca tcctgttcta tcccgccggc
1441 agcgaccgca cccccatcgt gttcgagggc ggcgaccgct cgctcaagtc cctgaccaag
1501 ttcatcaaga ccaacgccaa gatcccgtac gagctgccca agaagggctc cgacggcgac
1561 gagggcacct cggacgacaa ggacaagccc gcgtccgaca aggacgagct gtaagcggct
1621 atctgaacta ccccaggttt ggagcgtctg cttgcgcgct tgcgcttgca cactgtgcat
1681 ggatgggagt taaggaggag acggagcacg gaggctgcgc tcggttggtg gcttggagca
1741 ccggcagcgc gtgatccgtc ctggcagcag caacggcgga gcgggcgcat attggcgcga
1801 gctggcgagc ggctgttgct ggagaggata tgctgccggg cgggaggaag ggctaggggc
1861 agagatgaga gcgttacggg ctggcatgcg ggcgcccgtg cctctccctg cggtgcagtc
1921 cttgctagga gacgcacggt tttgccaaag agggacgctg tccacagccc tgcgactgga
1981 agttttttag gccctgcggt ggtagtggtg ttggtacggt tgtgtgcata agatgaacaa
2041 cgtttctctc aagacgagac tactagtatg ctgacggtgt gtgtatgtgg tggatggatt
2101 gtgccccgac catgaagagt gctgtgttgc ctcggcgctt ctgtcgccct ggatgtgcgt
2161 ggttccgaac gctggagtca tctgttgagg agcgagggtg ttgtcgggtc cgcccggcac
2221 ggccgcgtga tgtccggatg gggattgcga gcgagggcaa ccgcagcgca gatagcgccg
2281 cagcggatcg agctagcgca ggatgatgag agccgggcct tcgcggcgtg ggatcaggga
2341 ggagccaagg cggagtgcat gcgaggaaaa cagtgtgcgg caaagaacgg gctgcaagaa
2401 cgccttgcgc aaa
```

FIG. 2B

```
                    .         .         .         .250
CTT CTT TAC GGT AAC AAC ATC ATT ACA GGT GCT GTA ATC CCA ACT TCT AAC GCA ATC GGT
Leu Leu Tyr Gly Asn Asn Ile Ile Thr Gly Ala Val Ile Pro Thr Ser Asn Ala Ile Gly  90
                                Ser         Ile                 Ala
                    .         .         .300        .         .         .
CTT CAC TTC TAC CCA ATT TGG GAA GCT GCT TCT CTA GAC GAG TGG TTA TAC AAC GGT GGT
Leu His Phe Tyr Pro Ile Trp Glu Ala Ala Ser Leu Asp Glu Trp Leu Try Asn Gly Gly 110
                                            Val
                    .         .350      .         .         .         .
CCT TAC CAA CTT ATC GTT TGT CAC TTC CTT CTA GGT GTA TAC TGC TAC ATG GGT][CGT GAG
Pro Tyr Gln Leu Ile Val Cys His Phe Leu Leu Gly Val Tyr Cys Tyr Met Gly][Arg Glu 130
        Glu             Leu                     Ala
                    .400      .         .         .         .         .450
TGG GAA TTA TCT TTC CGT TTA GGT ATG CGT CCA TGG ATC GCT GTA GCT TAC TCA GCT CCA
Trp Glu Leu Ser Phe Arg Leu Gly Met Arg Pro Trp Ile Ala Val Ala Tyr Ser Ala Pro 150

                    .         .         .         .         .500      .
GTA GCT GCA GCT TCA GCT GTA TTC TTA GTT TAC CCT ATC GGC CAA GGT TCA TTC TCT GAC
Val Ala Ala Ala Ser Ala Val Phe Leu Val Tyr Pro Ile Gly Gln Gly Ser Phe Ser Asp 170
                Thr             Ile
                    .         .         .         .550      .         .
GGT ATG CCT TTA GGT][ATC TCT GGT ACT TTC AAC TTC ATG ATC GTA TTC CAA GCA GAA CAC
Gly Met Pro Leu Gly][Ile Ser Gly Thr Phe Asn Phe Met Ile Val Phe Gln Ala Glu His 190

                    .         .         .600      .         .         .
AAC ATC CTT ATG CAC CCA TTC CAC ATG TTA GGT GTT GCT GGT GTA TTC GGT GGT TCA TTA
Asn Ile Leu Met His Pro Phe His Met Leu Gly Val Ala Gly Val Phe Gly Gly Ser Leu 210

                    .         850       .         .         .         .
TTC TCA GCT ATG CAC GGT TCT TTA GTT ACT TCA TCT TTA ATC CGT GAA ACA ACT GAA AAC
Phe Ser Ala Met His Gly Ser Leu Val Thr Ser Ser Leu Ile Arg Glu Thr Thr Glu Asn 230
```

FIG. 3B

```
                .700      .         .          .          .        .750
GAA TCA GCT AAC GAA GGT TAC CGT TTC GGT CAA GAA GAA GAA ACT TAC AAC ATT GTA GCT
Glu Ser Ala Asn Glu Gly Tyr Arg Phe Gly Gln Glu Glu Glu Thr Tyr Asn Ile Val Ala 250

                .         .         .          .         .800          .
GCT CAT][GGT TAC TTT GGT CGT CTA ATC TTC CAA TAC GCT TCT TTC AAC AAC TCT CGT TCA
Ala His][Gly Tyr Phe Gly Arg Leu Ile Phe Gln Tyr Ala Ser Phe Asn Asn Ser Arg Ser 270

                .         .         .         .850        .          .
TTA CAC TTC TTC TTA GCT GCT TGG CCG GTA ATC GGT ATT TGG TTC ACT GCT TTA GGT TTA
Leu His Phe Phe Leu Ala Ala Trp Pro Val Ile Gly Ile Trp Phe Thr Ala Leu Gly Leu 290
                                        Val                             Ile
                .         .    .900          .         .         .
TCA ACT ATG GCA TTC AAC TTA AAC GGT TTC AAC TTC AAC CAA TCA GTA GTA GAC TCA CAA
Ser Thr Met Ala Phe Asn Leu Asn Gly Phe Asn Phe Asn Gln Ser Val Val Asp Ser Gln 310

                .        .950       .          .         .         .
GGT CGT GTA CTA AAC ACT TGG GCA GAC ATC ATC AAC CGT GCT AAC TTA GGT ATG GAA GTA
Gly Arg Val Leu Asn Thr Trp Ala Asp Ile Ile Asn Arg Ala Asn Leu Gly Met Glu Val 330
            Ile
            .1000     .         .          .         .        .1050
ATG CAC GAG CGT AAC GCT CAC AAC TTC CCT CTA GAC TTA GCT TCA ACT AAC TCT AGC TCA
Met His Glu Arg Asn Ala His Asn Phe Pro Leu Asp Leu Ala Ser Thr Asn Ser Ser Ser 350
                                                    Ala Ile Glu Ala Pro
                .      |--.------.-->  -->  .   <--  <---.1100----|.        .
AAC AAC TAA TTT TTTTTTAAACTAAAATAAATCTGGTTAACCATACCTAGTTTATTTTAGTTTATACACACTTTT
Asn Asn *Oc                                              S1
Thr     Gly     *Oc
     .       .      .1150     .       .
CATATATATATACTTAATAGCTACCATAGGCAGTTGGCAGGACGTCCC
```

FIG. 3C

```
  1 ATG GGC CAT CAT CAT CAT CAT CAT CAT CAT CAT CAC AGC AGC GGC CAT ATC GAA GGT CGT  60
  1 M   G   H   H   H   H   H   H   H   H   H   H   S   S   G   H   I   E   G   R    20

 61 CAT ATG GCG ACT ACT GAG TCC TCG GCC CCG GCG GCC ACC ACC CAG CCG GCC AGC ACC CCG  120
 21 H   M   A   T   T   E   S   S   A   P   A   A   T   T   Q   P   A   S   T   P    40

121 CTG GCG AAC TCG TCG CTG TAC GTC GGT GAC CTG GAG AAG GAT GTC ACC GAG GCC CAG CTG  180
 41 L   A   N   S   S   L   Y   V   G   D   L   E   K   D   V   T   E   A   Q   L    60

181 TTC GAG CTC TTC TCC TCG GTT GGC CCT GTG GCC TCC ATT CGC GTG TGC CGC GAT GCC GTC  240
 61 F   E   L   F   S   S   V   G   P   V   A   S   I   R   V   C   R   D   A   V    80

241 ACG CGC CGC TCG CTG GGC TAC GCC TAC GTC AAC TAC AAC AGC GCT CTG GAC CCC CAG GCT  300
 81 T   R   R   S   L   G   Y   A   Y   V   N   Y   N   S   A   L   D   P   Q   A    100

301 GCT GAC CGC GCC ATG GAG ACC CTG AAC TAC CAT GTC GTG AAC GGC AAG CCT ATG CGC ATC  360
101 A   D   R   A   M   E   T   L   N   Y   H   V   V   N   G   K   P   M   R   I    120

361 ATG TGG TCG CAC CGC GAC CCT TCG GCC CGC AAG TCG GGC GTC GGC AAC ATC TTC ATC AAG  420
121 M   W   S   H   R   D   P   S   A   R   K   S   G   V   G   N   I   F   I   K    140

421 AAC CTG GAC AAG ACC ATC GAC GCC AAG GCC CTG CAC GAC ACC TTC TCG GCC TTC GGC AAG  480
141 N   L   D   K   T   I   D   A   K   A   L   H   D   T   F   S   A   F   G   K    160

481 ATT CTG TCC TGC AAG GTT GCC ACT GAC GCC AAC GGC GTG TCG AAG GGC TAC GGC TTC GTG  540
161 I   L   S   C   K   V   A   T   D   A   N   G   V   S   K   G   Y   G   F   V    180

541 CAC TTC GAG GAC CAG GCC GCT GCC GAT CGC GCC ATT CAG ACC GTC AAC CAG AAG AAG ATT  600
181 H   F   E   D   Q   A   A   A   D   R   A   I   Q   T   V   N   Q   K   K   I    200

601 GAG GGC AAG ATC GTG TAC GTG GCC CCC TTC CAG AAG CGC GCT GAC CGC CCC AGG GCA AGG  660
201 E   G   K   I   V   Y   V   A   P   F   Q   K   R   A   D   R   P   R   A   R    220
```

FIG. 5A

```
 661 ACG TTG TAC ACC AAC GTG TTC GTC AAG AAC TTG CCG GCC GAC ATC GGC GAC GAC GAG CTG  720
 221 T   L   Y   T   N   V   F   V   K   N   L   P   A   D   I   G   D   D   E   L    240

 721 GGC AAG ATG GCC ACC GAG CAC GGC GAG ATC ACC AGC GCG GTG GTC ATG AAG GAC GAC AAG  780
 241 G   K   M   A   T   E   H   G   E   I   T   S   A   V   V   M   K   D   D   K    260

 781 GGC GGC AGC AAG GGC TTC GGC TTC ATC AAC TTC AAG GAC GCC GAG TCG GCG GCC AAG TGC  840
 261 G   G   S   K   G   F   G   F   I   N   F   K   D   A   E   S   A   A   K   C    280

 841 GTG GAG TAC CTG AAC GAG CGC GAG ATG AGC GGC AAG ACC CTG TAC GCC GGC CGC GCC CAG  900
 281 V   E   Y   L   N   E   R   E   M   S   G   K   T   L   Y   A   G   R   A   Q    300

 901 AAG AAG ACC GAG CGC GAG GCG ATG CTG CGC CAG AAG GCC GAG GAG AGC AAG CAG GAG CGT  960
 301 K   K   T   E   R   E   A   M   L   R   Q   K   A   E   E   S   K   Q   E   R    320

 961 TAC CTG AAG TAC CAG AGC ATG AAC CTG TAC GTC AAG AAC CTG TCC GAC GAG GAG GTC GAC  1020
 321 Y   L   K   Y   Q   S   M   N   L   Y   V   K   N   L   S   D   E   E   V   D    340

1021 GAC GAC GCC CTG CGT GAG CTG TTC GCC AAC TCT GGC ACC ATC ACC TCG TGC AAG GTC ATG  1080
 341 D   D   A   L   R   E   L   F   A   N   S   G   T   I   T   S   C   K   V   M    360

1081 AAG GAC GGC AGC GGC AAG TCC AAG GGC TTC GGC TTC GTG TGC TTC ACC AGC CAC GAC GAG  1140
 361 K   D   G   S   G   K   S   K   G   F   G   F   V   C   F   T   S   H   D   E    380

1141 GCC ACC CGG CCG CCC GTG ACC GAG ATG AAC GGC AAG ATG GTC AAG GGC AAG CCC CTG TAC  1200
 381 A   T   R   P   P   V   T   E   M   N   G   K   M   V   K   G   K   P   L   Y    400

1201 GTG GCC CTG GCG CAG CGC AAG GAC GTG CGC CGT GCC ACC CAG CTG GAG GCC AAC ATG CAG  1260
 401 V   A   L   A   Q   R   K   D   V   R   R   A   T   Q   L   E   A   N   M   Q    420

1261 GCG CGC ATG TAA GGATCC                                                            1278
 421 A   R   M   *                                                                     424
```

FIG. 5B

TS = transcription start and transcription stop

Bacterial luciferase A and B proteins expressed from a single mRNA containing the psbA 5' UTR with translational activator element.

SEQUENCE LISTING

```
<160> NUMBER OF SEQ ID NOS: 14

<210> SEQ ID NO 1
<211> LENGTH: 15
<212> TYPE: PRT
<213> ORGANISM: Chlamydomonas reinhardtii

<400> SEQUENCE: 1

Gln Tyr Gly Phe Val His Phe Glu Asp Gln Ala Ala Ala Asp Arg
  1               5                  10                  15


<210> SEQ ID NO 2
<211> LENGTH: 14
<212> TYPE: PRT
<213> ORGANISM: Chlamydomonas reinhardtii

<400> SEQUENCE: 2

Gly Phe Gly Phe Ile Asn Phe Lys Asp Ala Glu Ser Ala Ala
  1               5                  10


<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 3

cagtacggyt tcgtbcaytt cgaggaycag gc                                32


<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 4

ggaattcggy ttcggyttca tyaacttcaa ggaygcbgag                        40


<210> SEQ ID NO 5
<211> LENGTH: 2846
<212> TYPE: DNA
<213> ORGANISM: Chlamydomonas reinhardtii
<220> FEATURE:
<221> NAME/KEY: CDS
```

<222> LOCATION: (197)..(2065)

<400> SEQUENCE: 5
gaattcgcgg ccgctccgtg gttggtcctc atggtgtctt tttgaagagg acctgagcct 60
ttcacccaaa tatatcaaaa aacccgggca accggccaaa aaaattgcaa aagcctctcg 120
taggcacaaa agacctattc tagccatcaa ctttgtatcc gacgctgccg tttagctgcg 180
cgtcttgaag tcaagc atg gcg act act gag tcc tcg gcc ccg gcg gcc acc 232
Met Ala Thr Thr Glu Ser Ser Ala Pro Ala Ala Thr
1 5 10 acc cag ccg gcc agc acc ccg ctg gcg aac tcg tcg ctg tac gtc ggt 280
Thr Gln Pro Ala Ser Thr Pro Leu Ala Asn Ser Ser Leu Tyr Val Gly
15 20 25 gac ctg gag aag gat gtc acc gag gcc cag ctg ttc gag ctc ttc tcc 328
Asp Leu Glu Lys Asp Val Thr Glu Ala Gln Leu Phe Glu Leu Phe Ser
30 35 40 tcg gtt ggc cct gtg gcc tcc att cgc gtg tgc cgc gat gcc gtc acg 376
Ser Val Gly Pro Val Ala Ser Ile Arg Val Cys Arg Asp Ala Val Thr
45 50 55 60 cgc cgc tcg ctg ggc tac gcc tac gtc aac tac aac agc gct ctg gac 424
Arg Arg Ser Leu Gly Tyr Ala Tyr Val Asn Tyr Asn Ser Ala Leu Asp
65 70 75 ccc cag gct gct gac cgc gcc atg gag acc ctg aac tac cat gtc gtg 472
Pro Gln Ala Ala Asp Arg Ala Met Glu Thr Leu Asn Tyr His Val Val
80 85 90 aac ggc aag cct atg cgc atc atg tgg tcg cac cgc gac cct tcg gcc 520
Asn Gly Lys Pro Met Arg Ile Met Trp Ser His Arg Asp Pro Ser Ala
95 100 105 cgc aag tcg ggc gtc ggc aac atc ttc atc aag aac ctg gac aag acc 568
Arg Lys Ser Gly Val Gly Asn Ile Phe Ile Lys Asn Leu Asp Lys Thr
110 115 120 atc gac gcc aag gcc ctg cac gac acc ttc tcg gcc ttc ggc aag att 616
Ile Asp Ala Lys Ala Leu His Asp Thr Phe Ser Ala Phe Gly Lys Ile
125 130 135 140 ctg tcc tgc aag gtt gcc act gac gcc aac ggc gtg tcg aag ggc tac 664
Leu Ser Cys Lys Val Ala Thr Asp Ala Asn Gly Val Ser Lys Gly Tyr
145 150 155 ggc ttc gtg cac ttc gag gac cag gcc gct gcc gat cgc gcc att cag 712
Gly Phe Val His Phe Glu Asp Gln Ala Ala Ala Asp Arg Ala Ile Gln
160 165 170 acc gtc aac cag aag aag att gag ggc aag atc gtg tac gtg gcc ccc 760
Thr Val Asn Gln Lys Lys Ile Glu Gly Lys Ile Val Tyr Val Ala Pro
175 180 185 ttc cag aag cgc gct gac cgc ccc agg gca agg acg ttg tac acc aac 808
Phe Gln Lys Arg Ala Asp Arg Pro Arg Ala Arg Thr Leu Tyr Thr Asn
190 195 200 gtg ttc gtc aag aac ttg ccg gcc gac atc ggc gac gac gag ctg ggc 856
Val Phe Val Lys Asn Leu Pro Ala Asp Ile Gly Asp Asp Glu Leu Gly
205 210 215 220 aag atg gcc acc gag cac ggc gag atc acc agc gcg gtg gtc atg aag 904
Lys Met Ala Thr Glu His Gly Glu Ile Thr Ser Ala Val Val Met Lys
225 230 235 gac gac aag ggc ggc agc aag ggc ttc ggc ttc atc aac ttc aag gac 952
Asp Asp Lys Gly Gly Ser Lys Gly Phe Gly Phe Ile Asn Phe Lys Asp
240 245 250 gcc gag tcg gcg gcc aag tgc gtg gag tac ctg aac gag cgc gag atg 1000
Ala Glu Ser Ala Ala Lys Cys Val Glu Tyr Leu Asn Glu Arg Glu Met
255 260 265

-continued

```
agc ggc aag acc ctg tac gcc ggc cgc gcc cag aag aag acc gag cgc      1048
Ser Gly Lys Thr Leu Tyr Ala Gly Arg Ala Gln Lys Lys Thr Glu Arg
    270                 275                 280

gag gcg atg ctg cgc cag aag gcc gag gag agc aag cag gag cgt tac      1096
Glu Ala Met Leu Arg Gln Lys Ala Glu Glu Ser Lys Gln Glu Arg Tyr
285                 290                 295                 300

ctg aag tac cag agc atg aac ctg tac gtc aag aac ctg tcc gac gag      1144
Leu Lys Tyr Gln Ser Met Asn Leu Tyr Val Lys Asn Leu Ser Asp Glu
                305                 310                 315

gag gtc gac gac gac gcc ctg cgt gag ctg ttc gcc aac tct ggc acc      1192
Glu Val Asp Asp Asp Ala Leu Arg Glu Leu Phe Ala Asn Ser Gly Thr
            320                 325                 330

atc acc tcg tgc aag gtc atg aag gac ggc agc ggc aag tcc aag ggc      1240
Ile Thr Ser Cys Lys Val Met Lys Asp Gly Ser Gly Lys Ser Lys Gly
        335                 340                 345

ttc ggc ttc gtg tgc ttc acc agc cac gac gag gcc acc cgg ccg ccc      1288
Phe Gly Phe Val Cys Phe Thr Ser His Asp Glu Ala Thr Arg Pro Pro
    350                 355                 360

gtg acc gag atg aac ggc aag atg gtc aag ggc aag ccc ctg tac gtg      1336
Val Thr Glu Met Asn Gly Lys Met Val Lys Gly Lys Pro Leu Tyr Val
365                 370                 375                 380

gcc ctg gcg cag cgc aag gac gtg cgc cgt gcc acc cag ctg gag gcc      1384
Ala Leu Ala Gln Arg Lys Asp Val Arg Arg Ala Thr Gln Leu Glu Ala
                385                 390                 395

aac atg cag gcg cgc atg ggc atg ggc gcc atg agc cgc ccg ccg aac      1432
Asn Met Gln Ala Arg Met Gly Met Gly Ala Met Ser Arg Pro Pro Asn
            400                 405                 410

ccg atg gcc ggc atg agc ccc tac ccc ggc gcc atg ccg ttc ttc gct      1480
Pro Met Ala Gly Met Ser Pro Tyr Pro Gly Ala Met Pro Phe Phe Ala
        415                 420                 425

ccc ggc ccc ggc ggc atg gct gct ggc ccg cgc gct ccg ggc atg atg      1528
Pro Gly Pro Gly Gly Met Ala Ala Gly Pro Arg Ala Pro Gly Met Met
    430                 435                 440

tac ccg ccc atg atg ccg ccg cgc ggc atg cct ggc ccc ggc cgc ggc      1576
Tyr Pro Pro Met Met Pro Pro Arg Gly Met Pro Gly Pro Gly Arg Gly
445                 450                 455                 460

ccc cgc ggc ccc atg atg ccg ccc cag atg atg ggt ggc ccc atg atg      1624
Pro Arg Gly Pro Met Met Pro Pro Gln Met Met Gly Gly Pro Met Met
                465                 470                 475

ggc ccg ccc atg ggc ccc ggg cgc ggc cgt ggc ggc cgc ggc ccc tcc      1672
Gly Pro Pro Met Gly Pro Gly Arg Gly Arg Gly Gly Arg Gly Pro Ser
            480                 485                 490

ggc cgc ggc cag ggc cgc ggc aac aac gcc cct gcc cag cag ccc aag      1720
Gly Arg Gly Gln Gly Arg Gly Asn Asn Ala Pro Ala Gln Gln Pro Lys
        495                 500                 505

ccc gcc gct gag ccg gcc gcc gcg ccc gcc gcc gcc gcc ccc gct gcc      1768
Pro Ala Ala Glu Pro Ala Ala Ala Pro Ala Ala Ala Ala Pro Ala Ala
    510                 515                 520

gcg gcg cct gcc gcc gcg gcg gag ccg gag gcc ccc gcc gcc cag cag      1816
Ala Ala Pro Ala Ala Ala Ala Glu Pro Glu Ala Pro Ala Ala Gln Gln
525                 530                 535                 540

ccg ctg acc gcc tcc gcg ctg gcc gcc gcc gcg ccg gag cag cag aag      1864
Pro Leu Thr Ala Ser Ala Leu Ala Ala Ala Ala Pro Glu Gln Gln Lys
                545                 550                 555

atg atg atc ggc gag cgc ctg tac ccg cag gtg gcg gag ctg cag ccc      1912
Met Met Ile Gly Glu Arg Leu Tyr Pro Gln Val Ala Glu Leu Gln Pro
            560                 565                 570

gac ctg gct ggc aag atc acc ggc atg ctg ctg gag atg gac aac gcc      1960
Asp Leu Ala Gly Lys Ile Thr Gly Met Leu Leu Glu Met Asp Asn Ala
        575                 580                 585
```

-continued

```
gag ctt ctg atg ctt ctg gag tcg cac gag gcg ctg gtg tcc aag gtg     2008
Glu Leu Leu Met Leu Leu Glu Ser His Glu Ala Leu Val Ser Lys Val
    590                 595                 600

gac gag gcc atc gct gtg ctc aag cag cac aac gtg att gcc gag gag     2056
Asp Glu Ala Ile Ala Val Leu Lys Gln His Asn Val Ile Ala Glu Glu
605                 610                 615                 620

aac aag gct taaagcgcct gcacgcttgt gcgggctggt ggcgccggcg             2105
Asn Lys Ala


cgcgccggcg ctgcttgggc cgccggcagc atgggcgcgg cggacgcggt gtgggagcag   2165

tgcttgctgc ttctggccgc cgtgaagccg cgccgaactg gggcggacgg caggctggcg   2225

ttgacgccgg cgcgccacaa cacaaagttg gtggcgtgaa agtctctggg cgtgctccgg   2285

acggttgtaa ggttttaaga actggctttt ggccgggttg ccgcccaaag gcggaacggc   2345

ggtcttttca ggccaatcac atccggctgg aaaaattctt accaaagcca acccctgcac   2405

ccaaaaattt cgggttccga aagaacactc cccttttttc cggcaacgcg ttctttcaag   2465

gccaatcact ttccgggttg gaagaaaatg ttacccggaa aaggcgggaa gccccctgca   2525

cccggacaag ttattcgggg tttcgccggg aatgagcaag cgttcgggct gttggccgta   2585

tcgcgaacgc tgtcggggtg tcaggcgcca gaaggaagga tgacgttttg gtgaaggggt   2645

gcaaactgag cacacgagtt ttggcaatag acgtggagaa agtccagtgc ggggtgaggc   2705

ggatagcgga atcaagcgtg gcgggtccct ggcgagacga gacgcttctg ttgttttgct   2765

gagccctttg atggcacaat cgcactgttt tgagcaggcg actgtaaagt gcccgacgct   2825

aaaaaagcgg ccgcgaattc c                                              2846


<210> SEQ ID NO 6
<211> LENGTH: 15
<212> TYPE: PRT
<213> ORGANISM: Chlamydomonas reinhardtii

<400> SEQUENCE: 6

Trp Phe Val Asp Gly Glu Leu Ala Ser Asp Tyr Asn Gly Pro Arg
  1               5                  10                  15


<210> SEQ ID NO 7
<211> LENGTH: 22
<212> TYPE: PRT
<213> ORGANISM: Chlamydomonas reinhardtii

<400> SEQUENCE: 7

Gln Leu Ile Leu Trp Thr Thr Ala Asp Asp Leu Lys Ala Asp Ala Glu
  1               5                  10                  15

Ile Met Thr Val Phe Arg
             20


<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 8

cgcggatccg aygcbgagat yatgac                                            26
```

-continued

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 9

```
cgcgaattcg tcatratctc vgcrtc                                         26
```

<210> SEQ ID NO 10
<211> LENGTH: 2413
<212> TYPE: DNA
<213> ORGANISM: Chlamydomonas reinhardtii
<220> FEATURE:
<221> NAME/KEY: CDS
<222> LOCATION: (16)..(1614)

<400> SEQUENCE: 10

```
gagtacgttt acgcc atg aac cgt tgg aac ctt ctt gcc ctt acc ctg ggg      51
                 Met Asn Arg Trp Asn Leu Leu Ala Leu Thr Leu Gly
                   1               5                  10

ctg ctg ctg gtg gca gcg ccc ttc acc aag cac cag ttt gct cat gct       99
Leu Leu Leu Val Ala Ala Pro Phe Thr Lys His Gln Phe Ala His Ala
        15                  20                  25

tcc gat gag tat gag gac gac gag gag gac gat gcc ccc gcc gcc cct      147
Ser Asp Glu Tyr Glu Asp Asp Glu Glu Asp Asp Ala Pro Ala Ala Pro
    30                  35                  40

aag gac gac gac gtc gac gtt act gtg gtg acc gtc aag aac tgg gat      195
Lys Asp Asp Asp Val Asp Val Thr Val Val Thr Val Lys Asn Trp Asp
 45                  50                  55                  60

gag acc gtc aag aag tcc aag ttc gcg ctt gtg gag ttc tac gct cct      243
Glu Thr Val Lys Lys Ser Lys Phe Ala Leu Val Glu Phe Tyr Ala Pro
                65                  70                  75

tgg tgc ggc cac tgc aag acc ctc aag cct gag tac gct aag gct gcc      291
Trp Cys Gly His Cys Lys Thr Leu Lys Pro Glu Tyr Ala Lys Ala Ala
            80                  85                  90

acc gcc ctg aag gct gct gct ccc gat gcc ctt atc gcc aag gtc gac      339
Thr Ala Leu Lys Ala Ala Ala Pro Asp Ala Leu Ile Ala Lys Val Asp
        95                 100                 105

gcc acc cag gag gag tcc ctg gcc cag aag ttc ggc gtg cag ggc tac      387
Ala Thr Gln Glu Glu Ser Leu Ala Gln Lys Phe Gly Val Gln Gly Tyr
    110                 115                 120

ccc acc ctc aag tgg ttc gtt gat ggc gag ctg gct tct gac tac aac      435
Pro Thr Leu Lys Trp Phe Val Asp Gly Glu Leu Ala Ser Asp Tyr Asn
125                 130                 135                 140

ggc ccc cgc gac gct gat ggc att gtt ggc tgg gtg aag aag aag act      483
Gly Pro Arg Asp Ala Asp Gly Ile Val Gly Trp Val Lys Lys Lys Thr
                145                 150                 155

ggc ccc ccc gcc gtg acc gtt gag gac gcc gac aag ctg aag tcc ctg      531
Gly Pro Pro Ala Val Thr Val Glu Asp Ala Asp Lys Leu Lys Ser Leu
            160                 165                 170

gag gcg gac gct gag gtc gtt gtc gtc ggc tac ttc aag gcc ctg gag      579
Glu Ala Asp Ala Glu Val Val Val Val Gly Tyr Phe Lys Ala Leu Glu
        175                 180                 185

ggc gag atc tac gac acc ttc aag tcc tac gcc gcc aag acc gag gac      627
Gly Glu Ile Tyr Asp Thr Phe Lys Ser Tyr Ala Ala Lys Thr Glu Asp
    190                 195                 200

gtg gtg ttc gtg cag acc acc agc gcc gac gtc gcc aag gcc gcc ggc      675
Val Val Phe Val Gln Thr Thr Ser Ala Asp Val Ala Lys Ala Ala Gly
205                 210                 215                 220
```

-continued

```
ctg gac gcc gtg gac acc gtg tcc gtg gtc aag aac ttc gcc ggt gag      723
Leu Asp Ala Val Asp Thr Val Ser Val Val Lys Asn Phe Ala Gly Glu
                225                 230                 235

gac cgc gcc acc gcc gtc ctg gcc acg gac atc gac act gac tcc ctg      771
Asp Arg Ala Thr Ala Val Leu Ala Thr Asp Ile Asp Thr Asp Ser Leu
            240                 245                 250

acc gcg ttc gtc aag tcg gag aag atg ccc ccc acc att gag ttc aac      819
Thr Ala Phe Val Lys Ser Glu Lys Met Pro Pro Thr Ile Glu Phe Asn
        255                 260                 265

cag aag aac tct gac aag atc ttc aac agc ggc atc aac aag cag ctg      867
Gln Lys Asn Ser Asp Lys Ile Phe Asn Ser Gly Ile Asn Lys Gln Leu
    270                 275                 280

att ctg tgg acc acc gcc gac gac ctg aag gcc gac gcc gag atc atg      915
Ile Leu Trp Thr Thr Ala Asp Asp Leu Lys Ala Asp Ala Glu Ile Met
285                 290                 295                 300

act gtg ttc cgc gag gcc agc aag aag ttc aag ggc cag ctg gtg ttc      963
Thr Val Phe Arg Glu Ala Ser Lys Lys Phe Lys Gly Gln Leu Val Phe
                305                 310                 315

gtg acc gtc aac aac gag ggc gac ggc gcc gac ccc gtc acc aac ttc     1011
Val Thr Val Asn Asn Glu Gly Asp Gly Ala Asp Pro Val Thr Asn Phe
            320                 325                 330

ttc ggc ctc aag ggc gcc acc tcg cct gtg ctg ctg ggc ttc ttc atg     1059
Phe Gly Leu Lys Gly Ala Thr Ser Pro Val Leu Leu Gly Phe Phe Met
        335                 340                 345

gag aag aac aag aag ttc cgc atg gag ggc gag ttc acg gct gac aac     1107
Glu Lys Asn Lys Lys Phe Arg Met Glu Gly Glu Phe Thr Ala Asp Asn
    350                 355                 360

gtg gct aag ttc gcc gag agc gtg gtg gac ggc acc gcg cag gcc gtg     1155
Val Ala Lys Phe Ala Glu Ser Val Val Asp Gly Thr Ala Gln Ala Val
365                 370                 375                 380

ctc aag tcg gag gcc atc ccc gag gac ccc tat gag gat ggc gtc tac     1203
Leu Lys Ser Glu Ala Ile Pro Glu Asp Pro Tyr Glu Asp Gly Val Tyr
                385                 390                 395

aag att gtg ggc aag acc gtg gag tct gtg gtt ctg gac gag acc aag     1251
Lys Ile Val Gly Lys Thr Val Glu Ser Val Val Leu Asp Glu Thr Lys
            400                 405                 410

gac gtg ctg ctg gag gtg tac gcc ccc tgg tgc ggc cac tgc aag aag     1299
Asp Val Leu Leu Glu Val Tyr Ala Pro Trp Cys Gly His Cys Lys Lys
        415                 420                 425

ctg gag ccc atc tac aag aag ctg gcc aag cgc ttt aag aag gtg gat     1347
Leu Glu Pro Ile Tyr Lys Lys Leu Ala Lys Arg Phe Lys Lys Val Asp
    430                 435                 440

tcc gtc atc atc gcc aag atg gat ggc act gag aac gag cac ccc gag     1395
Ser Val Ile Ile Ala Lys Met Asp Gly Thr Glu Asn Glu His Pro Glu
445                 450                 455                 460

atc gag gtc aag ggc ttc cct acc atc ctg ttc tat ccc gcc ggc agc     1443
Ile Glu Val Lys Gly Phe Pro Thr Ile Leu Phe Tyr Pro Ala Gly Ser
                465                 470                 475

gac cgc acc ccc atc gtg ttc gag ggc ggc gac cgc tcg ctc aag tcc     1491
Asp Arg Thr Pro Ile Val Phe Glu Gly Gly Asp Arg Ser Leu Lys Ser
            480                 485                 490

ctg acc aag ttc atc aag acc aac gcc aag atc ccg tac gag ctg ccc     1539
Leu Thr Lys Phe Ile Lys Thr Asn Ala Lys Ile Pro Tyr Glu Leu Pro
        495                 500                 505

aag aag ggc tcc gac ggc gac gag ggc acc tcg gac gac aag gac aag     1587
Lys Lys Gly Ser Asp Gly Asp Glu Gly Thr Ser Asp Asp Lys Asp Lys
    510                 515                 520

ccc gcg tcc gac aag gac gag ctg taa gcggctatct gaactacccc           1634
Pro Ala Ser Asp Lys Asp Glu Leu
525                 530
```

-continued

```
aggtttggag cgtctgcttg cgcgcttgcg cttgcacact gtgcatggat gggagttaag   1694

gaggagacgg agcacggagg ctgcgctcgg ttggtggctt ggagcaccgg cagcgcgtga 1754

tccgtcctgg cagcagcaac ggcggagcgg gcgcatattg gcgcgagctg gcgagcggct   1814

gttgctggag aggatatgct gccgggcggg aggaagggct aggggcagag atgagagcgt 1874

tacgggctgg catgcgggcg cccgtgcctc tccctgcggt gcagtccttg ctaggagacg   1934

cacggttttg ccaaagaggg acgctgtcca cagccctgcg actggaagtt ttttaggccc   1994

tgcggtggta gtggtgttgg tacggttgtg tgcataagat gaacaacgtt tctctcaaga   2054

cgagactact agtatgctga cggtgtgtgt atgtggtgga tggattgtgc cccgaccatg   2114

aagagtgctg tgttgcctcg gcgcttctgt cgccctggat gtgcgtggtt ccgaacgctg   2174

gagtcatctg ttgaggagcg agggtgttgt cgggtccgcc cggcacggcc gcgtgatgtc   2234

cggatgggga ttgcgagcga gggcaaccgc agcgcagata gcgccgcagc ggatcgagct   2294

agcgcaggat gatgagagcc gggccttcgc ggcgtgggat cagggaggag ccaaggcgga   2354

gtgcatgcga ggaaaacagt gtgcggcaaa gaacgggctg caagaacgcc ttgcgcaaa    2413


<210> SEQ ID NO 11
<211> LENGTH: 4
<212> TYPE: PRT
<213> ORGANISM: Chlamydomonas reinhardtii

<400> SEQUENCE: 11

Cys Gly His Cys
  1


<210> SEQ ID NO 12
<211> LENGTH: 4
<212> TYPE: PRT
<213> ORGANISM: Chlamydomonas reinhardtii

<400> SEQUENCE: 12

Lys Asp Glu Leu
  1


<210> SEQ ID NO 13
<211> LENGTH: 1424
<212> TYPE: DNA
<213> ORGANISM: Chlamydomonas reinhardtii
<220> FEATURE:
<221> NAME/KEY: CDS
<222> LOCATION: (252)..(1310)
<220> FEATURE:
<221> NAME/KEY: misc_feature
<222> LOCATION: (279)
<223> OTHER INFORMATION: Codon also can encode Ser
<220> FEATURE:
<221> NAME/KEY: misc_feature
<222> LOCATION: (282)
<223> OTHER INFORMATION: Codon also can encode Glu
<220> FEATURE:
<221> NAME/KEY: misc_feature
<222> LOCATION: (294)
<223> OTHER INFORMATION: Codon also can encode Gly
<220> FEATURE:
<221> NAME/KEY: misc_feature
<222> LOCATION: (306)
<223> OTHER INFORMATION: Codon also can encode Asn
<220> FEATURE:
<221> NAME/KEY: misc_feature
<222> LOCATION: (357)
<223> OTHER INFORMATION: Codon also can encode Leu
<220> FEATURE:
<221> NAME/KEY: misc_feature
<222> LOCATION: (369)
```

-continued

<223> OTHER INFORMATION: Codon also can encode Thr
<220> FEATURE:
<221> NAME/KEY: misc_feature
<222> LOCATION: (486)
<223> OTHER INFORMATION: Codon also can encode Ser
<220> FEATURE:
<221> NAME/KEY: misc_feature
<222> LOCATION: (495)
<223> OTHER INFORMATION: Codon also can encode Ile
<220> FEATURE:
<221> NAME/KEY: misc_feature
<222> LOCATION: (510)
<223> OTHER INFORMATION: Codon also can encode Ala
<220> FEATURE:
<221> NAME/KEY: misc_feature
<222> LOCATION: (555)
<223> OTHER INFORMATION: Codon also can encode Val
<220> FEATURE:
<221> NAME/KEY: misc_feature
<222> LOCATION: (588)
<223> OTHER INFORMATION: Codon also can encode Glu
<220> FEATURE:
<221> NAME/KEY: misc_feature
<222> LOCATION: (600)
<223> OTHER INFORMATION: Codon also can encode Leu
<220> FEATURE:
<221> NAME/KEY: misc_feature
<222> LOCATION: (621)
<223> OTHER INFORMATION: Codon also can encode Ala
<220> FEATURE:
<221> NAME/KEY: misc_feature
<222> LOCATION: (714)
<223> OTHER INFORMATION: Codon also can encode Thr
<220> FEATURE:
<221> NAME/KEY: misc_feature
<222> LOCATION: (729)
<223> OTHER INFORMATION: Codon also can encode Ile
<220> FEATURE:
<221> NAME/KEY: misc_feature
<222> LOCATION: (1092)
<223> OTHER INFORMATION: Codon also can encode Val
<220> FEATURE:
<221> NAME/KEY: misc_feature
<222> LOCATION: (1191)
<223> OTHER INFORMATION: Codon also can encode Ile
<220> FEATURE:
<221> NAME/KEY: misc_feature
<222> LOCATION: (1284)
<223> OTHER INFORMATION: Codon also can encode Ala
<220> FEATURE:
<221> NAME/KEY: misc_feature
<222> LOCATION: (1287)
<223> OTHER INFORMATION: Codon also can encode Ile
<220> FEATURE:
<221> NAME/KEY: misc_feature
<222> LOCATION: (1290)
<223> OTHER INFORMATION: Codon also can encode Glu
<220> FEATURE:
<221> NAME/KEY: misc_feature
<222> LOCATION: (1293)
<223> OTHER INFORMATION: Codon also can encode Ala
<220> FEATURE:
<221> NAME/KEY: misc_feature
<222> LOCATION: (1296)
<223> OTHER INFORMATION: Codon also can encode Pro
<220> FEATURE:
<221> NAME/KEY: misc_feature
<222> LOCATION: (1302)
<223> OTHER INFORMATION: Codon also can encode Thr
<220> FEATURE:
<221> NAME/KEY: misc_feature
<222> LOCATION: (1308)
<223> OTHER INFORMATION: Codon also can encode Gly

<400> SEQUENCE: 13
cgtcctattt taatactccg aaggaggcag ttggcaggca actgccactg acgtcccgta 60
agggtaaggg gacgtccact ggcgtcccgt aaggggaagg ggacgtaggt acataaatgt 120

-continued

```
gctaggtaac taacgtttga ttttttgtgg tataatatat gtaccatgct tttaatagaa    180

gcttgaattt ataaattaaa atatttttac aatattttac ggagaaatta aaactttaaa    240

aaaattaaca t atg aca gca att tta gaa cgt cgt gaa aat tct agc cta     290
             Met Thr Ala Ile Leu Glu Arg Arg Glu Asn Ser Ser Leu
               1               5                  10

tgg gct cgt ttt tgt gag tgg atc act tca act gaa aac cgt tta tac      338
Trp Ala Arg Phe Cys Glu Trp Ile Thr Ser Thr Glu Asn Arg Leu Tyr
     15                  20                  25

atc ggt tgg ttc ggt gta atc atg atc cca tgt ctt ctt act gca aca      386
Ile Gly Trp Phe Gly Val Ile Met Ile Pro Cys Leu Leu Thr Ala Thr
 30                  35                  40                  45

tca gta ttc atc atc gct ttc atc gct gct ccg cca gta gac atc gat      434
Ser Val Phe Ile Ile Ala Phe Ile Ala Ala Pro Pro Val Asp Ile Asp
                 50                  55                  60

ggt atc cgt gaa cca gtt tca ggt tct ctt ctt tac ggt aac aac atc      482
Gly Ile Arg Glu Pro Val Ser Gly Ser Leu Leu Tyr Gly Asn Asn Ile
             65                  70                  75

att aca ggt gct gta atc cca act tct aac gca atc ggt ctt cac ttc      530
Ile Thr Gly Ala Val Ile Pro Thr Ser Asn Ala Ile Gly Leu His Phe
         80                  85                  90

tac cca att tgg gaa gct gct tct cta gac gag tgg tta tac aac ggt      578
Tyr Pro Ile Trp Glu Ala Ala Ser Leu Asp Glu Trp Leu Tyr Asn Gly
     95                 100                 105

ggt cct tac caa ctt atc gtt tgt cac ttc ctt cta ggt gta tac tgc      626
Gly Pro Tyr Gln Leu Ile Val Cys His Phe Leu Leu Gly Val Tyr Cys
110                 115                 120                 125

tac atg ggt cgt gag tgg gaa tta tct ttc cgt tta ggt atg cgt cca      674
Tyr Met Gly Arg Glu Trp Glu Leu Ser Phe Arg Leu Gly Met Arg Pro
                130                 135                 140

tgg atc gct gta gct tac tca gct cca gta gct gca gct tca gct gta      722
Trp Ile Ala Val Ala Tyr Ser Ala Pro Val Ala Ala Ala Ser Ala Val
            145                 150                 155

ttc tta gtt tac cct atc ggc caa ggt tca ttc tct gac ggt atg cct      770
Phe Leu Val Tyr Pro Ile Gly Gln Gly Ser Phe Ser Asp Gly Met Pro
        160                 165                 170

tta ggt atc tct ggt act ttc aac ttc atg atc gta ttc caa gca gaa      818
Leu Gly Ile Ser Gly Thr Phe Asn Phe Met Ile Val Phe Gln Ala Glu
    175                 180                 185

cac aac atc ctt atg cac cca ttc cac atg tta ggt gtt gct ggt gta      866
His Asn Ile Leu Met His Pro Phe His Met Leu Gly Val Ala Gly Val
190                 195                 200                 205

ttc ggt ggt tca tta ttc tca gct atg cac ggt tct tta gtt act tca      914
Phe Gly Gly Ser Leu Phe Ser Ala Met His Gly Ser Leu Val Thr Ser
                210                 215                 220

tct tta atc cgt gaa aca act gaa aac gaa tca gct aac gaa ggt tac      962
Ser Leu Ile Arg Glu Thr Thr Glu Asn Glu Ser Ala Asn Glu Gly Tyr
            225                 230                 235

cgt ttc ggt caa gaa gaa gaa act tac aac att gta gct gct cat ggt     1010
Arg Phe Gly Gln Glu Glu Glu Thr Tyr Asn Ile Val Ala Ala His Gly
        240                 245                 250

tac ttt ggt cgt cta atc ttc caa tac gct tct ttc aac aac tct cgt     1058
Tyr Phe Gly Arg Leu Ile Phe Gln Tyr Ala Ser Phe Asn Asn Ser Arg
    255                 260                 265

tca tta cac ttc ttc tta gct gct tgg ccg gta atc ggt att tgg ttc     1106
Ser Leu His Phe Phe Leu Ala Ala Trp Pro Val Ile Gly Ile Trp Phe
270                 275                 280                 285

act gct tta ggt tta tca act atg gca ttc aac tta aac ggt ttc aac     1154
Thr Ala Leu Gly Leu Ser Thr Met Ala Phe Asn Leu Asn Gly Phe Asn
                290                 295                 300
```

-continued

```
ttc aac caa tca gta gta gac tca caa ggt cgt gta cta aac act tgg      1202
Phe Asn Gln Ser Val Val Asp Ser Gln Gly Arg Val Leu Asn Thr Trp
            305                 310                 315

gca gac atc atc aac cgt gct aac tta ggt atg gaa gta atg cac gag      1250
Ala Asp Ile Ile Asn Arg Ala Asn Leu Gly Met Glu Val Met His Glu
        320                 325                 330

cgt aac gct cac aac ttc cct cta gac tta gct tca act aac tct agc      1298
Arg Asn Ala His Asn Phe Pro Leu Asp Leu Ala Ser Thr Asn Ser Ser
    335                 340                 345

tca aac aac taa ttttttttta aactaaaata aatctggtta accataccta          1350
Ser Asn Asn
350

gtttatttta gtttatacac acttttcata tatatatact taatagctac cataggcagt    1410

tggcaggacg tccc                                                      1424


<210> SEQ ID NO 14
<211> LENGTH: 1278
<212> TYPE: DNA
<213> ORGANISM: Chlamydomonas reinhardtii
<220> FEATURE:
<221> NAME/KEY: CDS
<222> LOCATION: (1)..(1272)

<400> SEQUENCE: 14

atg ggc cat cat cat cat cat cat cat cat cat cac agc agc ggc cat        48
Met Gly His His His His His His His His His His Ser Ser Gly His
  1               5                  10                  15

atc gaa ggt cgt cat atg gcg act act gag tcc tcg gcc ccg gcg gcc        96
Ile Glu Gly Arg His Met Ala Thr Thr Glu Ser Ser Ala Pro Ala Ala
            20                  25                  30

acc acc cag ccg gcc agc acc ccg ctg gcg aac tcg tcg ctg tac gtc       144
Thr Thr Gln Pro Ala Ser Thr Pro Leu Ala Asn Ser Ser Leu Tyr Val
        35                  40                  45

ggt gac ctg gag aag gat gtc acc gag gcc cag ctg ttc gag ctc ttc       192
Gly Asp Leu Glu Lys Asp Val Thr Glu Ala Gln Leu Phe Glu Leu Phe
    50                  55                  60

tcc tcg gtt ggc cct gtg gcc tcc att cgc gtg tgc cgc gat gcc gtc       240
Ser Ser Val Gly Pro Val Ala Ser Ile Arg Val Cys Arg Asp Ala Val
 65                  70                  75                  80

acg cgc cgc tcg ctg ggc tac gcc tac gtc aac tac aac agc gct ctg       288
Thr Arg Arg Ser Leu Gly Tyr Ala Tyr Val Asn Tyr Asn Ser Ala Leu
                85                  90                  95

gac ccc cag gct gct gac cgc gcc atg gag acc ctg aac tac cat gtc       336
Asp Pro Gln Ala Ala Asp Arg Ala Met Glu Thr Leu Asn Tyr His Val
            100                 105                 110

gtg aac ggc aag cct atg cgc atc atg tgg tcg cac cgc gac cct tcg       384
Val Asn Gly Lys Pro Met Arg Ile Met Trp Ser His Arg Asp Pro Ser
        115                 120                 125

gcc cgc aag tcg ggc gtc ggc aac atc ttc atc aag aac ctg gac aag       432
Ala Arg Lys Ser Gly Val Gly Asn Ile Phe Ile Lys Asn Leu Asp Lys
    130                 135                 140

acc atc gac gcc aag gcc ctg cac gac acc ttc tcg gcc ttc ggc aag       480
Thr Ile Asp Ala Lys Ala Leu His Asp Thr Phe Ser Ala Phe Gly Lys
145                 150                 155                 160

att ctg tcc tgc aag gtt gcc act gac gcc aac ggc gtg tcg aag ggc       528
Ile Leu Ser Cys Lys Val Ala Thr Asp Ala Asn Gly Val Ser Lys Gly
                165                 170                 175

tac ggc ttc gtg cac ttc gag gac cag gcc gct gcc gat cgc gcc att       576
Tyr Gly Phe Val His Phe Glu Asp Gln Ala Ala Ala Asp Arg Ala Ile
            180                 185                 190
```

-continued

```
cag acc gtc aac cag aag aag att gag ggc aag atc gtg tac gtg gcc        624
Gln Thr Val Asn Gln Lys Lys Ile Glu Gly Lys Ile Val Tyr Val Ala
        195                 200                 205

ccc ttc cag aag cgc gct gac cgc ccc agg gca agg acg ttg tac acc        672
Pro Phe Gln Lys Arg Ala Asp Arg Pro Arg Ala Arg Thr Leu Tyr Thr
    210                 215                 220

aac gtg ttc gtc aag aac ttg ccg gcc gac atc ggc gac gac gag ctg        720
Asn Val Phe Val Lys Asn Leu Pro Ala Asp Ile Gly Asp Asp Glu Leu
225                 230                 235                 240

ggc aag atg gcc acc gag cac ggc gag atc acc agc gcg gtg gtc atg        768
Gly Lys Met Ala Thr Glu His Gly Glu Ile Thr Ser Ala Val Val Met
                245                 250                 255

aag gac gac aag ggc ggc agc aag ggc ttc ggc ttc atc aac ttc aag        816
Lys Asp Asp Lys Gly Gly Ser Lys Gly Phe Gly Phe Ile Asn Phe Lys
            260                 265                 270

gac gcc gag tcg gcg gcc aag tgc gtg gag tac ctg aac gag cgc gag        864
Asp Ala Glu Ser Ala Ala Lys Cys Val Glu Tyr Leu Asn Glu Arg Glu
        275                 280                 285

atg agc ggc aag acc ctg tac gcc ggc cgc gcc cag aag aag acc gag        912
Met Ser Gly Lys Thr Leu Tyr Ala Gly Arg Ala Gln Lys Lys Thr Glu
    290                 295                 300

cgc gag gcg atg ctg cgc cag aag gcc gag gag agc aag cag gag cgt        960
Arg Glu Ala Met Leu Arg Gln Lys Ala Glu Glu Ser Lys Gln Glu Arg
305                 310                 315                 320

tac ctg aag tac cag agc atg aac ctg tac gtc aag aac ctg tcc gac       1008
Tyr Leu Lys Tyr Gln Ser Met Asn Leu Tyr Val Lys Asn Leu Ser Asp
                325                 330                 335

gag gag gtc gac gac gac gcc ctg cgt gag ctg ttc gcc aac tct ggc       1056
Glu Glu Val Asp Asp Asp Ala Leu Arg Glu Leu Phe Ala Asn Ser Gly
            340                 345                 350

acc atc acc tcg tgc aag gtc atg aag gac ggc agc ggc aag tcc aag       1104
Thr Ile Thr Ser Cys Lys Val Met Lys Asp Gly Ser Gly Lys Ser Lys
        355                 360                 365

ggc ttc ggc ttc gtg tgc ttc acc agc cac gac gag gcc acc cgg ccg       1152
Gly Phe Gly Phe Val Cys Phe Thr Ser His Asp Glu Ala Thr Arg Pro
    370                 375                 380

ccc gtg acc gag atg aac ggc aag atg gtc aag ggc aag ccc ctg tac       1200
Pro Val Thr Glu Met Asn Gly Lys Met Val Lys Gly Lys Pro Leu Tyr
385                 390                 395                 400

gtg gcc ctg gcg cag cgc aag gac gtg cgc cgt gcc acc cag ctg gag       1248
Val Ala Leu Ala Gln Arg Lys Asp Val Arg Arg Ala Thr Gln Leu Glu
                405                 410                 415

gcc aac atg cag gcg cgc atg taa ggatcc                                1278
Ala Asn Met Gln Ala Arg Met
            420
```

RNA BINDING PROTEIN AND BINDING SITE USEFUL FOR EXPRESSION OF RECOMBINANT MOLECULES

This is a stage application filed under 35 USC 371, of PCT/US98/00840, filed Jan. 16, 1998. This application claims benefit of provisional No. 60/035,955 filed Jan. 17, 1997 and provisional appln No. 60/069,400 filed Dec. 12, 1997.

This invention was made with government support under Contract No. GM 54659 by the National Institutes of Health and Contract No. DO-FG03-93ER20116 by the U.S. Department of Energy. The government has certain rights in the invention.

TECHNICAL FIELD

The invention relates to expression systems and methods for expression of desired genes and gene products in cells. Particularly, the invention relates to a gene encoding a RNA binding protein useful for regulating gene expression in cells, the protein binding site, a gene encoding a regulating protein disulfide isomerase and methods and systems for gene expression of recombinant molecules.

BACKGROUND

Expression systems for expression of exogenous foreign genes in eukaryotic and prokaryotic cells are basic components of recombinant DNA technology. Despite the abundance of expression systems and their wide-spread use, they all have characteristic disadvantages. For example, while expression in *E. coli* is probably the most popular as it is easy to grow and is well understood, eukaryotic proteins expressed therein are not properly modified. Moreover, those proteins tend to precipitate into insoluble aggregates and are difficult to obtain in large amounts. Mammalian expression systems, while practical on small-scale protein production, are more difficult, time-consuming and expensive than in *E. coli.*

A number of plant expression systems exist as well as summarized in U.S. Pat. No. 5,234,834, the disclosures of which are hereby incorporated by reference. One advantage of plants or algae in an expression system is that they can be used to produce pharmacologically important proteins and enzymes on a large scale and in relatively pure form. In addition, micro-algae have several unique characteristics that make them ideal organisms for the production of proteins on a large scale. First, unlike most systems presently used to produce transgenic proteins, algae can be grown in minimal media (inorganic salts) using sunlight as the energy source. These algae can be grown in contained fermentation vessels or on large scale in monitored ponds. Ponds of up to several acres are routinely used for the production of micro-algae. Second, plants and algae have two distinct compartments, the cytoplasm and the chloroplast, in which proteins can be expressed. The cytoplasm of algae is similar to that of other eukaryotic organisms used for protein expression, like yeast and insect cell cultures. The chloroplast is unique to plants and algae and proteins expressed in this environment are likely to have properties different from those of cytoplasmically expressed proteins.

The present invention describes an expression system in which exogenous molecules are readily expressed in either prokaryotic or eukaryotic hosts and in either the cytoplasm or chloroplast. These beneficial attributes are based on the discovery and cloning of components of translation regulation in plants as described in the present invention.

Protein translation plays a key role in the regulation of gene expression across the spectrum of organisms (Kozak, *Ann. Rev. Cell Biol.,* 8:197–225 (1992) and de Smit and Van Duin, *Prog. Nucleic Acid Res. Mol. Biol.,* 38:1–35 (1990)). The majority of regulatory schemes characterized to date involve translational repression often involving proteins binding to mRNA to limit ribosome association (Winter et al., *Proc. Natl. Acad. Sci., USA,* 84:7822–7826 (1987) and Tang and Draper, *Biochem.,* 29:4434–4439 (1990)). Translational activation has also been observed (Wulczyn and Kahmann, *Cell,* 65:259–269 (1991)), but few of the underlying molecular mechanisms for this type of regulation have been identified. In plants, light activates the expression of many genes. Light has been shown to activate expression of specific chloroplast encoded mRNAs by increasing translation initiation (Mayfield et al., *Ann. Rev. Plant Physiol. Plant Mol. Biol.,* 46:147–166 (1995) and Yohn et al., *Mol. Cell Biol.,* 16:3560–3566 (1996)). Genetic evidence in higher plants and algae has shown that nuclear encoded factors are required for translational activation of specific chloroplast encoded mRNAs (Rochaix et al., *Embo J.,* 8:1013–1021 (1989), Kuchka et al., *Cell,* 58:869–876 (1989), Girard-Bascou et al., *Embo J.,* 13:3170–3181 (1994), Kim et al., *Plant Mol. Biol.,* 127:1537–1545 (1994).

In the green algae *Chlamydomonas reinhardtii,* a number of nuclear mutants have been identified that affect translation of single specific mRNAs in the chloroplast, often acting at translation initiation (Yohn et al., *supra,* (1996)). Mutational analysis of chloroplast mRNAs has identified sequence elements within the 5' untranslated region (UTR) of mRNAs that are required for translational activation (Mayfield et al., *supra,* (1995), Mayfield et al., *J. Cell Biol.,* 127:1537–1545 (1994) and Rochaix, *Ann. Rev. Cell Biol.,* 8:1–28 (1992)), and the 5' UTR of a chloroplast mRNA can confer a specific translation phenotype on a reporter gene in vivo (Zerges and Rochaix, *Mol. Cell Biol.,* 14:5268–5277 (1994) and Staub and Maliga, *Embo J.,* 12:601–606 (1993).

Putative translational activator proteins were identified by purifying a complex of four proteins that binds with high affinity and specificity to the 5' UTR of the chloroplast encoded psbA mRNA [encoding the D1 protein, a major component of Photosystem II (PS II)] (Danon and Mayfield, *Embo J.,* 10:3993–4001 (1991)). Binding of these proteins to the 5' UTR of psbA mRNA correlates with translation of this mRNA under a variety of physiological (Danon and Mayfield, *id.,* (1991)) and biochemical conditions (Danon and Mayfield, *Science,* 266:1717–1719 (1994) and Danon and Mayfield, *Embo J.,* 13:2227–2235 (1994)), and in different genetic backgrounds (Yohn et al., *supra,* (1996)). The binding of this complex to the psbA mRNA can be regulated in vitro in response to both redox potential (Danon and Mayfield, *Science,* 266:1717–1719 (1994)) and phosphorylation (Danon and Mayfield, *Embo J.,* 13:2227–2235 (1994)), both of which are thought to transduce the light signal to activate translation of psbA mRNA. The 47 kDa member of the psbA RNA binding complex (RB47) is in close contact with the RNA, and antisera specific to this protein inhibits binding to the psbA mRNA in vitro (Danon and Mayfield, *supra,* (1991)).

Although the translational control of psbA mRNA by RB47 has been reported, the protein has not been extensively characterized and the gene encoding RB47 has not been identified, cloned and sequenced. In addition, the regulatory control of the activation of RNA binding activity to the binding site by nuclear-encoded trans-acting factors, such as RB60, have not been fully understood. The present invention now describes the cloning and sequencing of both RB47 and RB60. Based on the translation regulation mechanisms of RB47 and RB60 with the RB47 binding site, the present invention also describes a translation regulated expression system for use in both prokaryotes and eukaryotes.

BRIEF DESCRIPTION OF THE INVENTION

The RB47 gene encoding the RB47 activator protein has now been cloned and sequenced, and the target binding site for RB47 on messenger RNA (mRNA) has now been identified. In addition, a regulatory protein disulfide isomerase, a 60 kilodalton protein referred to as RB60, has also been cloned, sequenced and characterized. Thus, the present invention is directed to gene expression systems in eukaryotic and prokaryotic cells based on translational regulation by RB47 protein, its binding site and the RB60 regulation of RB47 binding site activation.

More particularly, the present invention describes the use of the RB47 binding site, i.e., a 5' untranslated region (UTR) of the chloroplast psbA gene, in the context of an expression system for regulating the expression of genes encoding a desired recombinant molecule. Protein translation is effected by the combination of the RB47 binding site and the RB47 binding protein in the presence of protein translation components. Regulation can be further imposed with the use of the RB60 regulatory protein disulfide isomerase. Therefore, the present invention describes reagents and expression cassettes for controlling gene expression by affecting translation of a coding nucleic acid sequence in a cell expression system.

Thus, in one embodiment, the invention contemplates a RB47 binding site sequence, i.e., a mRNA sequence, typically a mRNA leader sequence, which contains the RB47 binding site. A preferred RB47 binding site is psbA mRNA. For use in expressing recombinant molecules, the RB47 binding site is typically inserted 5' to the coding region of the preselected molecule to be expressed. In a preferred embodiment, the RB47 binding site is inserted into the 5' untranslated region along with an upstream psbA promoter to drive the expression of a preselected nucleic acid encoding a desired molecule. In alternative embodiments, the RB47 binding site is inserted into the regulatory region downstream of any suitable promoter present in a eukaryotic or prokaryotic expression vector. Preferably, the RB47 binding site is positioned within 100 nucleotides of the translation initiation site. In a further aspect, 3' to the coding region is a 3' untranslated region (3' UTR) necessary for transcription termination and RNA processing.

Thus, in a preferred embodiment, the invention contemplates an expression cassette or vector that contains a transcription unit constructed for expression of a preselected nucleic acid or gene such that upon transcription, the resulting mRNA contains the RB47 binding site for regulation of the translation of the preselected gene transcript through the binding of the activating RB47 protein. The RB47 protein is provided endogenously in a recipient cell and/or is a recombinant protein expressed in that cell.

Thus, the invention also contemplates a nucleic acid molecule containing the sequence of the RB47 gene. The nucleic acid molecule is preferably in an expression vector capable of expressing the gene in a cell for use in interacting with a RB47 binding site. The invention therefore contemplates an expressed recombinant RB47 protein. In one embodiment, the RB47 binding site and RB47 encoding nucleotide sequences are provided on the same genetic element. In alternative embodiments, the RB47 binding site and RB47 encoding nucleotide sequences are provided separately.

The invention further contemplates a nucleic acid molecule containing the sequence encoding the 69 kilodalton precursor to RB47. In alternative embodiments, the RB47 nucleic acid sequence contains a sequence of nucleotides to encode a histidine tag. Thus, the invention relates to the use of recombinant RB47, precursor RB47, and histidine-modified RB47 for use in enhancing translation of a desired nucleic acid.

The invention further contemplates a nucleic acid molecule containing a nucleotide sequence of a polypeptide which regulates the binding of RB47 to RB47 binding site. A preferred regulatory molecule is the protein disulfide isomerase RB60. The RB60-encoding nucleic acid molecule is preferably in an expression vector capable of expressing the gene in a cell for use in regulating the interaction of RB47 with a RB47 binding site. Thus, the invention also contemplates an expressed recombinant RB60 protein. In one embodiment, the RB47 binding site, RB47 encoding and RB60 encoding nucleotide sequences are provided on the same genetic element. In alternative embodiments, the expression control nucleotide sequences are provided separately. In a further aspect, the RB60 gene and RB47 binding site sequence are provided on the same construct.

The invention can therefore be a cell culture system, an in vitro expression system or a whole tissue, preferably a plant, in which the transcription unit is present that contains the RB47 binding site and further includes a (1) transcription unit capable of expressing RB47 protein or (2) the endogenous RB47 protein itself for the purpose of enhancing translation of the preselected gene having an RB47 binding site in the mRNA. Preferred cell culture systems are eukaryotic and prokaryotic cells. Particularly preferred cell culture systems include plants and more preferably algae.

A further preferred embodiment includes (1) a separate transcription unit capable of expressing a regulatory molecule, preferably RB60 protein, or (2) the endogenous RB60 protein itself for the purpose of regulating translation of the preselected gene having an RB47 binding site in the mRNA. In an alternative preferred embodiment, one transcription unit is capable of expressing both the RB47 and RB60 proteins. In a further aspect, the RB47 binding site sequence and RB60 sequence are provided on the same construct.

In one aspect of the present invention, plant cells endogenously containing RB47 and RB60 proteins are used for the expression of recombinant molecules, such as proteins or polypeptides, through activation of the RB47 binding in an exogenously supplied expression cassette. Alternatively, stable plant cell lines containing endogenous RB47 and RB60 are first generated in which RB47 and/or RB60 proteins are overexpressed. Overexpression is obtained preferably through the stable transformation of the plant cell with one or more expression cassettes for encoding recombinant RB47 and RB60. In a further embodiment, stable cell lines, such as mammalian or bacterial cell lines, lacking endogenous RB47 and/or RB60 proteins are created that express exogenous RB47 and/or RB60.

Plants for use with the present invention can be a transgenic plant, or a plant in which the genetic elements of the invention have been introduced. Based on the property of controlled translation provided by the combined use of the RB47 protein and the RB47 binding site, translation can be regulated for any gene product, and the system can be introduced into any plant species. Similarly, the invention is useful for any prokaryotic or eukaryotic cell system.

Methods for the preparation of expression vectors is well known in the recombinant DNA arts, and for expression in plants is well known in the transgenic plant arts. These particulars are not essential to the practice of the invention, and therefore will not be considered as limiting.

The invention allows for high level of protein synthesis in plant chloroplasts and in the cytoplasm of both prokaryotic and eukaryotic cells. Because the chloroplast is such a productive plant organ, synthesis in chloroplasts is a preferred site of translation by virtue of the large amounts of protein that can be produced. This aspect provides for great advantages in agricultural production of mass quantities of a preselected protein product.

The invention further provides for the ability to screen for agonists or antagonists of the binding of RB47 to the RB47 binding site using the expression systems as described herein. Antagonists of the binding are useful in the prevention of plant propagation.

Also contemplated by the present invention is a screening assay for agonists or antagonists of RB60 in a manner analogous to that described above for RB47. Such agonists or antagonists would be useful in general to modify expression of RB60 as a way to regulate cellular processes in a redox manner.

Kits containing expression cassettes and expression systems, along with packaging materials comprising a label with instructions for use, as described in the claimed embodiments are also contemplated for use in practicing the methods of this invention.

Other uses will be apparent to one skilled in the art in light of the present disclosures.

BRIEF DESCRIPTION OF DRAWINGS

In the figures forming a portion of this disclosure:

FIGS. 1A–1D show the complete protein amino acid residue sequence of RB47 is shown from residues 1–623, together with the corresponding nucleic acid sequence encoding the RB47 sequence, from base 1 to base 2732. The nucleotide coding region is shown from base 197–2065, the precursor form. The mature form is from nucleotide position 197–1402. Also shown is the mRNA leader, bases 1–196, and poly A tail of the mRNA, bases 2066–2732. Both the nucleotide and amino acid sequence are listed in SEQ ID NO 5.

FIGS. 2A–2B show the complete protein amino acid residue sequence of RB60 is shown from residues 1–488, together with the corresponding nucleic acid sequence from base 1 to base 2413, of which bases 16–1614 encode the RB60 sequence. Both the nucleotide and amino acid sequence are listed in SEQ ID NO 10.

FIGS. 3A–3C show the complete sequence of the psbA mRNA, showing both encoded psbA protein amino acid residue sequence (residues 1–352) and the nucleic acid sequence as further described in Example 3 is illustrated. Both the nucleotide and amino acid sequence are listed in SEQ ID NO 13.

FIGS. 5A–5B show the nucleotide and amino acid sequence of the RB47 molecule containing a histidine tag, the sequences of which are also listed in SEQ ID NO 14.

2. Cloning of RB60

Figure 3A:
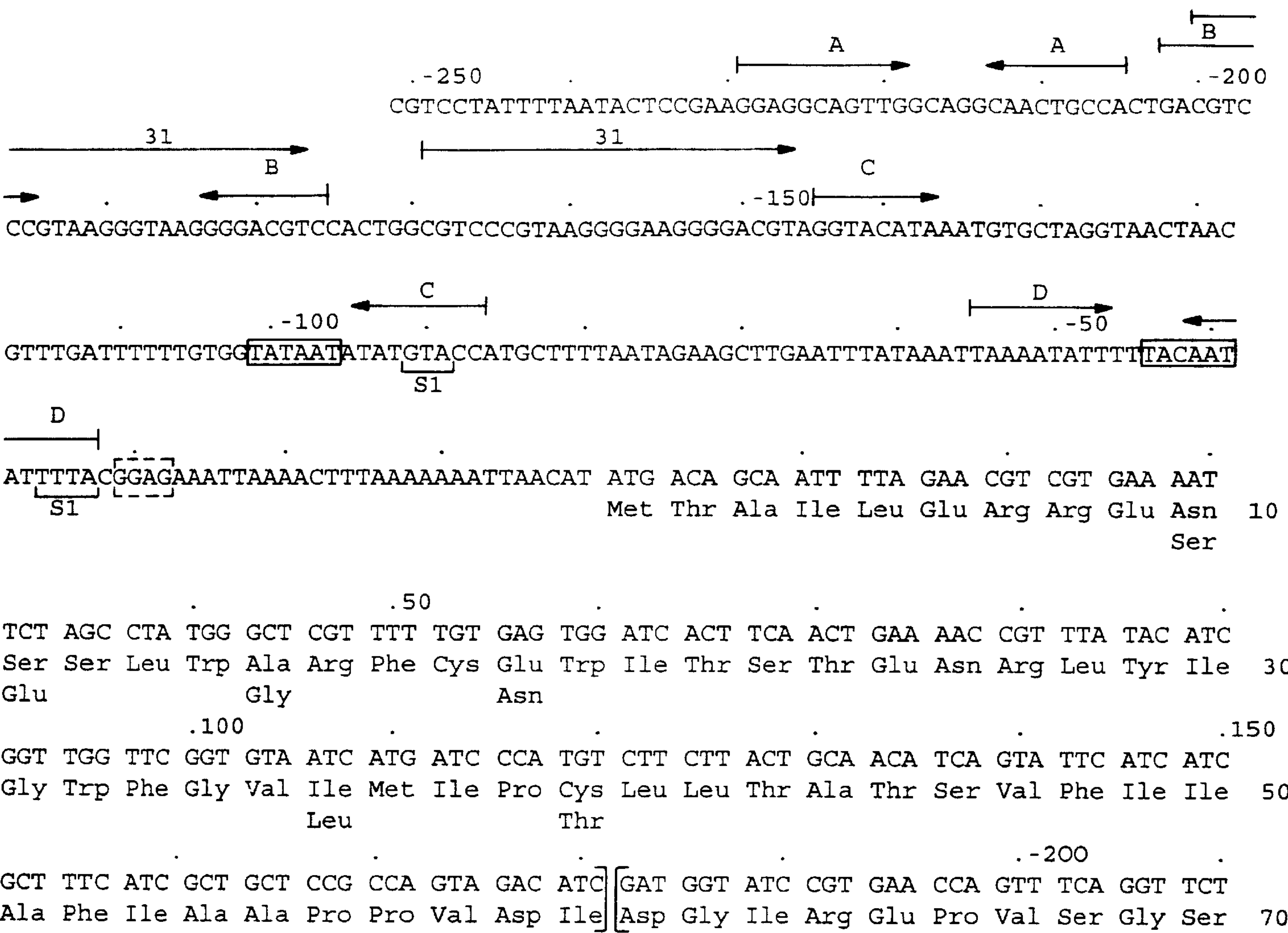

To clone the cDNA encoding the 60 kDa psbA mRNA binding protein (RB60), the psbA-specific RNA binding proteins were purified from light-grown *C. reinhardtii* cells using heparin-agarose chromatography followed by psbA RNA affinity chromatography (RAC). RAC-purified proteins were separated by two-dimensional polyacrylamide gel electrophoresis. The region corresponding to RB60 was isolated from the PVDF membrane. RB60 protein was then digested with trypsin. Unambiguous amino acid sequences were obtained from two peptide tryptic fragments (WFVDGELASDYNGPR (SEQ ID NO 6) and (QLILWTTADDLKADAEIMTVFR (SEQ ID NO 7)) as described above for RB47. The calculated molecular weights of the two tryptic peptides used for further analysis precisely matched with the molecular weights determine by mass spectrometry. The DNA sequence corresponding to one peptide of 22 amino acid residues was amplified by PCR using degenerate oligonucleotides, the forward primer 5'CGCGGATCCGAYGCBGAGATYATGAC3' (SEQ ID NO 8) and the reverse primer 5'CGCGAATTCGTCATRATCTCVGCRTC3' (SEQ ID NO 9), where R can be A or G (the other IUPAC nucleotides have been previously defined above). The amplified sequence was then used to screen a λ-gt10 cDNA library from *C. reinhardtii.* Three clones were identified with the largest being 2.2 kb. Selection and sequencing was performed as described for RB47 cDNA.

The resulting RB60 cDNA sequence is available via GenBank (Accession Number AF027727). The nucleotide and encoded amino acid sequence of RB60 is also shown in FIGS. 2A–2B (SEQ ID NO 10). The protein coding sequence of 488 amino acid residues corresponds to nucleotide positions 16–1614 of the 2413 base pair sequence. The predicted amino acid sequence of the cloned cDNA contained the complete amino acid sequences of the two tryptic peptides. The amino acid sequence of the encoded protein revealed that it has high sequence homology to both plant and mammalian protein disulfide isomerase (PDI), and contains the highly conserved thioredoxin-like domains with —CysGlyHisCys— (—CGHC—) (SEQ ID NO 11) catalytic sites in both the N-terminal and C-terminal regions and the —LysAspGluLeu— (—KDEL—) (SEQ ID NO 12) endoplasmic reticulum (ER) retention signal at the C-terminus found in all PDIs. PDI is a mutifunctional protein possessing enzymatic activities for the formation, reduction, and isomerization of disulfide bonds during protein folding, and is typically found in the ER. The first 30 amino acid residues of RB60 were found to lack sequence homology with the N-terminal signal sequence of PDI from plants or mammalian cells. However, this region has characteristics of chloroplast transit peptides of *C. reinhardtii,* which have similarities with both mitochondrial and higher plant chloroplast presequences. A transit peptide sequence should override the function of the —KDEL— ER retention signal and target the protein to the chloroplast since the —KDEL— signal acts only to retain the transported protein in the ER.

3. Preparation of psbA Promoter Sequence and RB47 Binding Site Nucleotide Sequence The chloroplast psbA gene from the green unicellular alga *C. reinhardii* was cloned and sequenced as described by Erickson et al., *Embo J.,* 3:2753–2762 (1984), the disclosure of which is hereby incorporated by reference. The DNA sequence of the coding regions and the 5' and 3' untranslated (UTR) flanking sequences of the *C. reinhardii* psbA gene is shown in FIGS. 3A–3C. The psbA gene sequence is also available through GenBank as further discussed in Example 4. The nucleotide sequence is also listed as SEQ ID NO 13. The deduced amino acid sequence (also listed in SEQ ID NO 13) of the coding region is shown below each codon beginning with the first methionine in the open reading frame. Indicated in the 5' non-coding sequence are a putative Shine-Dalgarno sequence in the dotted box, two putative transcription initiation sites determined by S1 mapping (S1) and the Pribnow-10 sequence in the closed box. Inverted repeats of eight or more base pairs are marked with arrows and labeled A–D. A direct repeat of 31 base pairs with only two mismatches is marked with arrows labeled 31. Indicated in the 3' non-coding sequence is a large inverted repeat marked by a forward arrow and the SI cleavage site marking the 3' end of the mRNA. Both the 5' and 3' untranslated regions are used in preparing one of the expression cassettes of this invention as further described below.

The 5' UTR as previously discussed contains both the psbA promoter and the RB47 binding site. The nucleotide sequence defining the psbA promoter contains the region of the psbA DNA involved in binding of RNA polymerase to initiate transcription. The −10 sequence component of the psbA promoter is indicated by the boxed nucleotide sequence upstream of the first S1 while the −35 sequence is located approximately 35 bases before the putative initiation site. As shown in FIGS. 3A–3C, the −10 sequence is boxed, above which is the nucleotide position (−100) from the first translated codon. The −35 sequence is determined accordingly. A psbA promoter for use in an expression cassette of this invention ends at the first indicated S1 site (nucleotide position −92 as counting from the first ATG) in FIGS. 3A–3C and extends to the 5' end (nucleotide position −251 as shown in FIGS. 3A–3C). Thus, the promoter region is 160 bases in length. A more preferred promoter region extends at least 100 nucleotides to the 5' end from the S1 site. A most preferred region contains nucleotide sequence ending at the s1 site and extending 5' to include the −35 sequence, i.e., from −92 to −130 as counted from the first encoded amino acid residue (39 bases).

The psbA RB47 binding site region begins at the first S1 site as shown in FIGS. 3A–3C and extends to the first adenine base of the first encoded methionine residue. Thus, a psbA RB47 binding site in the psbA gene corresponds to the nucleotide positions from −91 to −1 as shown in FIG. 3A–3C.

The above-identified regions are used to prepare expression constructs as described below. The promoter and RB47 binding site regions can be used separately; for example, the RB47 binding site sequence can be isolated and used in a eukaryotic or prokaryotic plasmid with a non-psbA promoter. Alternatively, the entire psbA 5' UTR having 251 nucleotides as shown in FIGS. 3A–3C is used for the regulatory region in an expression cassette containing both the psbA promoter and RB47 binding site sequence as described below.

4. Preparation of Expression Vectors and Expression of Coding Sequences

A. Constructs Containing an psbA Promoter, an RB47 Binding Site Nucleotide Sequence, a Desired Heterologous Coding Sequence, an RB47-Encoding Sequence and an RB60-Encoding Sequence Plasmid expression vector constructs, alternatively called plasmids, vectors, constructs and the like, are constructed containing various combinations of elements of the present invention as described in the following examples. Variations of the positioning and operably linking of the genetic elements described in the present invention and in the examples below are contemplated for use in practicing the methods of this invention. Methods for manipulating DNA elements into operable expression cassettes are well known in the art of molecular biology. Accordingly, variations of control elements, such as constitutive or inducible promoters, with respect to prokaryotic or eukaryotic expression systems as described in Section C. are contemplated herein although not enumerated. Moreover, the expression the various elements is not limited to one transcript producing one mRNA; the invention contemplates protein expression from more than one transcript if desired.

As such, while the examples below recite one or two types of expression cassettes, the genetic elements of RB47 binding site, any desired coding sequence, in combination with RB47 and RB60 coding sequences along with a promoter are readily combined in a number of operably linked permeations depending on the requirements of the cell system selected for the expression. For example, for expression in a chloroplast, endogenous RB47 protein is present therefore an expression cassette having an RB47 binding site and a desired coding sequence is minimally required along with an operative promoter sequence. Overexpression of RB47 may be preferable to enhance the translation of the coding sequence; in that case, the chloroplast is further transformed with an expression cassette containing an RB47-encoding sequence. Although the examples herein and below utilize primarily the sequence encoding the precursor form of RB47, any of the RB47-encoding sequences described in the present invention, i.e., RB47 precursor, mature RB47 and histidine-modified RB47 are contemplated for use in any expression cassette and system as described herein. To regulate the activation of translation, an RB60-encoding element is provided to the expression system to provide the ability to regulate redox potential in the cell as taught in Section B. These examples herein and below represent a few of the possible permutations of genetic elements for expression in the methods of this invention.

In one embodiment, a plasmid is constructed containing an RB47 binding site directly upstream of an inserted coding region for a heterologous protein of interest, and the RB47 and RB60 coding regions. Heterologous refers to the nature of the coding region being dissimilar and not from the same gene as the regulatory molecules in the plasmid, such as RB47 and RB60. Thus, all the genetic elements of the present invention are produced in one transcript from the IPTG-inducible psbA promoter. Alternative promoters are similarly acceptable.

The final construct described herein for use in a prokaryotic expression system makes a single mRNA from which all three proteins are translated. The starting plasmid is any *E. coli* based plasmid containing an origin of replication and selectable marker gene. For this example, the Bluescript plasmid, pBS, commercially available through Stratagene, Inc., La Jolla, Calif., which contains a polylinker-cloning site and an ampicilin resistant marker is selected for the vector.

The wild-type or native psbA gene (Erickson et al., *Embo J.,* 3:2753–2762 (1984), also shown in FIGS. 3A–3C, is cloned into pBS at the EcoRI and BamHI sites of the polylinker. The nucleotide sequence of the psbA gene is available on GenBank with the 5' UTR and 3' UTR respectively listed in Accession Numbers X01424 and X02350. The EcoRI site of psbA is 1.5 kb upstream of the psbA initiation codon and the BamHI site is 2 kb downstream of the stop codon. This plasmid is referred to as pDl.

Using site-directed PCR mutagenesis, well known to one of ordinary skill in the art, an NdeI site is placed at the initiation codon of psbA in the pDl plasmid so that the ATG of the NdeI restriction site is the ATG initiation codon. This plasmid is referred to as pDl/Nde. An Nde site is then placed at the initiation codon of the gene encoding the heterologous protein of interest and an Xho I site is placed directly downstream (within 10 nucleotides) of the TAA stop codon of the heterologous protein coding sequence. Again using site-directed mutagenesis, an XhoI site is placed within 10 nucleotides of the initiation codon of RB47, the preparation of which is described in Example 2, and an NotI site is placed directly downstream of the stop codon of RB47. The heterologous coding region and the RB47 gene are then ligated into pDl/Nde so that the heterologous protein gene is directly adjacent to the RB47 binding site and the RB47 coding region is downstream of the heterologous coding region, using the Xho I site at the heterologous stop codon and the Not I site of the pDl polylinker.

These genetic manipulations result in a plasmid containing the 5' end of the psbA gene including the promoter region and with the RB47 binding site immediately upstream of a heterologous coding region, and the RB47 coding region immediately downstream of the heterologous coding region. The nucleotides between the stop codon of the heterologous coding region and the initiation codon of the RB47 coding region is preferably less than 20 nucleotides and preferably does not contain any additional stop codons in any reading frame. This plasmid is referred to as pD1/RB47.

Figure 4:
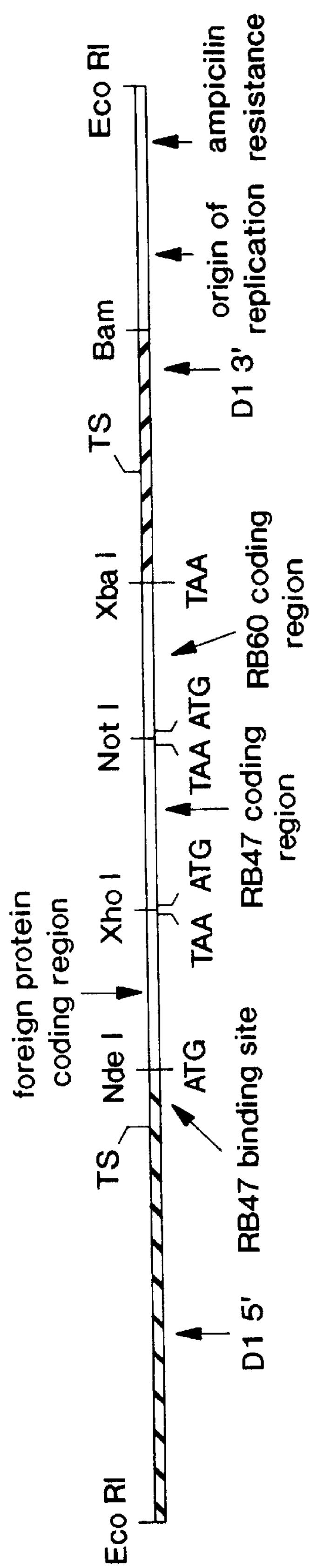
FIG. 4 is a schematic diagram of an expression cassette containing on one transcription unit from 5' to 3', a promoter region derived from the psbA gene for encoding the D1 protein from *C. reinhardtii* further containing a transcription initiation site (TS), the RB47 binding site, a region for insertion of a foreign or heterologous coding region, a RB47 coding region, a RB60 coding region, and the 3' flanking region containing transcription termination site (TS), flanked by an origin of replication and selection marker. Restriction endonuclease sites for facilitating insertion of the independent genetic elements are indicated and further described in Example 4A.

Using site-directed mutagenesis, a NotI site is placed immediately (within 10 nucleotides) upstream of the initiation codon of RB60, the preparation of which is described in Example 2, and an Xba I site is placed downstream of the RB60 stop codon. This DNA fragment is then ligated to the 3' end of the psbA gene using the Xba I site found in the 3' end of the psbA gene so that the psbA 3' end is downstream of the RB60 coding region. This fragment is then ligated into the pD1/RB47 plasmid using the NotI and BamHI sites so that the RB60 coding region directly follows the RB47 coding region. The resulting plasmid is designated pD1/RB47/RB60. Preferably there is less then 20 nucleotides between the RB47 and RB60 coding regions and preferably there are no stop codons in any reading frame in that region. The final plasmid thus contains the following genetic elements operably linked in the 5' to 3' direction: the 5' end of the psbA gene with a promoter capable of directing transcription in chloroplasts, an RB47 binding site, a desired heterologous coding region, the RB47 coding region, the RB60 coding region, and the 3' end of the psbA gene which contains a transcription termination and mRNA processing site, and an *E. coli* origin of replication and amplicillin resistance gene. A diagram of this plasmid with the restriction sites is shown in FIG. 4.

Expression of pD1/RB47/RB60 in *E. coli* to produce recombinant RB47, RB60 and the recombinant heterologous protein is performed as described in Example 4B. The heterologous protein is then purified as further described.

Expression cassettes in which the sequences encoding RB47 and RB60 are similarly operably linked to a heterologous coding sequence having the psbA RB47 binding site as described in Example 3 are prepared with a different promoter for use in eukaryotic, such as mammalian expression systems. In this aspect, the cassette is similarly prepared as described above with the exception that restriction cloning sites are dependent upon the available multiple cloning sites in the recipient vector. Thus, the RB47 binding site prepared in Example 3 is prepared for directed ligation into a selected expression vector downstream of the promoter in that vector. The RB47 and RB60 coding sequences are obtained from the pD1/RB47/RB60 plasmid by digestion with XhoI and XbaI and inserted into a similarly digested vector if the sites are present. Alternatively, site-directed mutagenesis is utilized to create appropriate linkers. A desired heterologous coding sequence is similarly ligated into the vector for expression.

B. Constructs Containing RB47 Nucleotide Sequence

1) Purified Recombinant RB47 Protein

In one approach to obtain purified recombinant RB47 protein, the full length RB47 cDNA prepared above was cloned into the *E. coli* expression vector pET3A (Studier et al., *Methods Enzymol.,* 185:60–89 (1990)), also commercially available by Novagen, Inc., Madison, Wis. and transformed into BL21 *E. coli* cells. The cells were grown to a density of 0.4 ($OD_{600}$), then induced with 0.5 mM IPTG. Cells were then allowed to grow for an additional 4 hours, at which point they were pelleted and frozen.

Confirmation of the identity of the cloned cDNA as encoding the authentic RB47 protein was accomplished by examining protein expressed from the cDNA by immunoblot analysis and by RNA binding activity assay. The recombinant RB47 protein produced when the RB47 cDNA was expressed was recognized by antisera raised against the *C. reinhardtii* RB47 protein. The *E. coli* expressed protein migrated at 80 kDa on SDS-PAGE, but the protein was actually 69 kDa, as determined by mass spectrometry of the *E. coli* expressed protein. This mass agrees with the mass predicted from the cDNA sequence. A 60 kDa product was also produced in *E. coli,* and recognized by the antisera against the *C. reinhardtii* protein, which is most likely a degradation or early termination product of the RB47 cDNA. The recombinant RB47 protein expressed from the RB47 cDNA is recognized by the antisera raised against the *C. reinhardtii* protein at levels similar to the recognition of the authentic *C. reinhardtii* RB47 protein, demonstrating that the cloned cDNA produces a protein product that is immunologically related to the naturally produced RB47 protein. In order to generate a recombinant equivalent of the endogenous native RB47, the location of the 47 kDa polypeptide was mapped on the full-length recombinant protein by comparing mass spectrometric data of tryptic digests of the *C. reinhardtii* 47 kDa protein and the full-length recombinant protein. Thus, peptide mapping by mass spectrometry has shown that the endogenous RB47 protein corresponds primarily to the RNA binding domains contained within the N-terminal region of the predicted precursor protein, suggesting that a cleavage event is necessary to produce the mature 47 kDa protein. Thus, full-length recombinant RB47 is 69 kDa and contains a carboxy domain that is cleaved in vivo to generate the endogenous mature form of RB47 that is 47 kDa.

To determine if the heterologously expressed RB47 protein was capable of binding the psbA RNA, the *E. coli* expressed protein was purified by heparin agarose chromatography. The recombinant RB47 protein expressed in *E. coli* was purified using a protocol similar to that used previously for purification of RB47 from *C. reinhardtii.* Approximately 5 g of *E. coli* cells grown as described above were resuspended in low salt extraction buffer (10 mM Tris [pH 7.5], 10 mM NaCl, 10 mM $MgCl_2$, 5 mM β-mercaptoethanol) and disrupted by sonication. The soluble cell extract was applied to a 5 mL Econo-Pac heparin cartridge (Bio-Rad) which was washed prior to elution of the RB47 protein (Danon and Mayfield, *Embo J.,* 10:3993–4001 (1991)).

The *E. coli* expressed protein that bound to the heparin agarose matrix was eluted from the column at the same salt concentration as used to elute the authentic *C. reinhardtii* RB47 protein. This protein fraction was used in in vitro binding assays with the psbA 5' UTR. Both the 69 and 60 kDa *E. coli* expressed proteins crosslinked to the radiolabeled psbA 5' UTR at levels similar to crosslinking of the endogenous RB47 protein, when the RNA/protein complex is subjected to UV irradiation.

Heparin agarose purified proteins, both from the *E. coli* expressed RB47 cDNA and from *C. reinhardtii* cells, were used in an RNA gel mobility shift assay to determine the relative affinity and specificity of these proteins for the 5' UTR of the psbA mRNA. The *E. coli* expressed proteins bound to the psbA 5' UTR in vitro with properties that are similar to those of the endogenous RB47 protein purified from *C. reinhardtii.* RNA binding to both the *E. coli* expressed and the endogenous RB47 protein was competed using either 200 fold excess of unlabeled psbA RNA or *200* fold excess of poly(A) RNA. RNA binding to either of these proteins was poorly competed using 200 fold excess of total RNA or 200 fold excess of the 5' UTR of the psbD or psbC RNAs. Different forms of the RB47 protein (47 kDa endogenous protein vs. the 69 kDa *E. coli* expressed protein) may account for the slight differences in mobility observed when comparing the binding profiles of purified *C. reinhardtii* protein to heterologously expressed RB47.

The mature form of RB47 is also produced in recombinant form by the insertion by PCR of an artificial stop codon in the RB47 cDNA at nucleotide positions 1403–1405 with a stop codon resulting in a mature RB47 recombinant protein having 402 amino acids as shown in FIGS. 1A–1D. An example of this is shown in FIGS. 5A–5B for the production of a recombinant histidine-modified RB47 mature protein as described below. The complete RB47 cDNA is inserted into an expression vector, such as pET3A as described above, for expression of the mature 47 kDa form of the RB47 protein. In the absence of the inserted stop codon, the transcript reads through to nucleotide position 2066–2068 at the TAA stop codon to produce the precursor RB47 having the above-described molecular weight characteristics and 623 amino acid residues.

Recombinant RB47 is also expressed and purified in plant cells. For this aspect, *C. reinhardtii* strains were grown in complete media (Tris-acetate-phosphate [TAP] (Harris, *The Chlamydonas Sourcebook,* San Diego, Calif., Academic Press (1989)) to a density of $5\times10^6$ cells/mL under constant light. Cells were harvested by centrifugation at 4° C. for 5 minutes at 4,000 g. Cells were either used immediately or frozen in liquid $N_2$ for storage at −70° C.

Recombinant RB47 protein was also produced as a modified RB47 protein with a histidine tag at the amino-terminus according to well known expression methods using pET19-D vectors available from Novagen, Inc., Madison, Wis. The nucleotide and amino acid sequence of a recombinant histidine-modified RB47 of the mature 47 kDa form is shown in FIGS. 5A–5B with the nucleotide and amino acid sequence also listed in SEQ ID NO 14. Thus the nucleotide sequence of a histidine-modified RB47 is 1269 bases in length. The precursor form of the RB47 protein is similarly obtained in the expression system, both of which are modified by the presence of a histidine tag that allows for purification by metal affinity chromatography.

The recombinant histidine-modified RB47 purified through addition of a poly-histidine tag followed by $Ni^{+2}$ column chromatography showed similar binding characteristics as that described for recombinant precursor RB47 described above.

C. Constructs Containing RB60 Nucleotide Sequence

In one approach to obtain purified recombinant RB60 protein, the full-length RB60 cDNA prepared above was cloned into the *E. coli* expression vector pET3A (Studier et al., *Methods Enzymol.,* 185:60–89 (1990)), also commercially available by Novagen, Inc., Madison, Wis. and transformed into BL21 *E. coli* cells. The cells were grown to a density of 0.4 ($OD_{600}$), then induced with 0.5 mM IPTG. Cells were then allowed to grow for an additional 4 hours, at which point they were pelleted and frozen.

Recombinant histidine-modified RB60 was also expressed with a pET19-D vector as described above for RB47 that was similarly modified. Purification of the recombinant RB60 proteins was performed as described for RB47 thereby producing recombinant RB60 proteins for use in the present invention.

The RB60 coding sequence is also mutagenized for directional ligation into an selected vector for expression in alternative systems, such as mammalian expression systems.

D. Constructs Containing an RB47-Encoding Sequence and an RB60-Encoding Sequence To prepare an expression cassette for encoding both RB47 and RB60, one approach is to digest plasmid pD1/RB47/RB60 prepared above with XhoI and XbaI to isolate the fragment for both encoding sequences. The fragment is then inserted into a similarly digested expression vector if available or is further mutagenized to prepare appropriate restriction sites.

Alternatively, the nucleotide sequences of RB47 and RB60, as described in Example 2, are separately prepared for directional ligation into a selected vector.

An additional embodiment of the present invention is to prepare an expression cassette containing the RB47 binding site along with the coding sequences for RB47 and RB60, the plasmid pD1/RB47/RB60 prepared above is digested with NdeI and XhoI to prepare an expression cassette in which any desired coding sequence having similarly restriction sites is directionally ligated. Expression vectors containing both the RB47 and RB60 encoding sequences in which the RB47 binding site sequence is utilized with a different promoter are also prepared as described in Example 4A.

E. Constructs Containing an RB47 Binding Site Nucleotide Sequence, Insertion Sites for a Desired Heterologous Coding Sequence, and an RB47-Encoding Sequence In another permutation, a plasmid or expression cassette is constructed containing an RB47 binding site directly upstream of an inserted coding region for a heterologous protein of interest, and the RB47 coding region. The final construct described herein for use in a prokaryotic expression system makes a single mRNA from which both proteins are translated.

Figure 6:
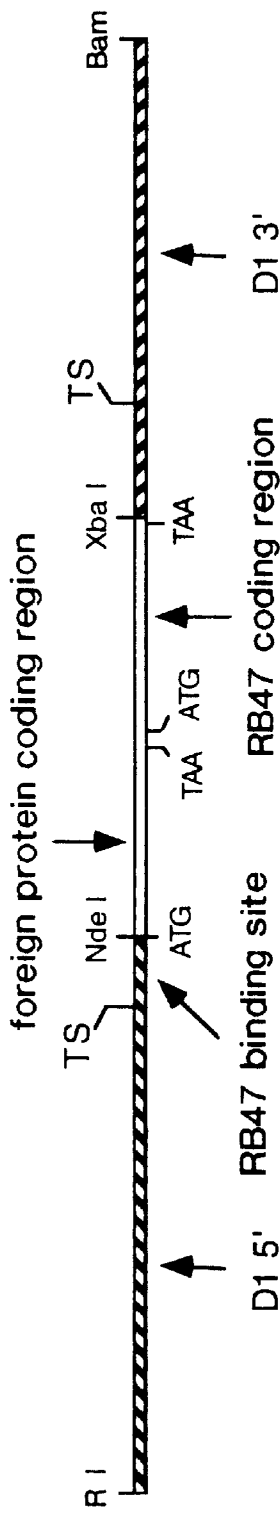
FIG. 6 is a schematic diagram of an expression cassette containing on one transcription unit from 5' to 3', a promoter region derived from the psbA gene for encoding the D1 protein from *C. reinhardtii* further containing a transcription initiation site (TS), the RB47 binding site, a region for RB47 is also shown in FIGS. 1A–1D (SEQ ID NO 5). As described in Section 2 above, the predicted protein sequence from the cloned cDNA contained both the derived peptide sequences of RB47 and is highly homologous to poly(A) binding proteins (PABP) from a variety of eukaryotic organisms.

The plasmid referred to as pD1/RB47 is prepared as described above in Example 4A. A diagram of this plasmid with the restriction sites is shown in FIG. 6.

Expression of pD1/RB47 in *E. coli* to produce recombinant RB47 and the recombinant heterologous protein is performed as described in above. The heterologous protein is then purified as further described.

To produce an expression cassette that allows for insertion of an alternative desired coding sequence, the plasmid pD1/RB47 is digested with NdeI and XhoI resulting in a vector having restriction endonuclease sites for insertion of a desired coding sequence operably linked to a RB47 binding site and RB47 coding sequence on one transcriptional unit.

F. Constructs Containing an RB47 Binding Site Nucleotide Sequence, Insertion Sites for a Desired Heterologous Coding Sequence, and an RB47-Encoding Sequence In another permutation, a plasmid or expression cassette is constructed containing an RB47 binding site directly upstream of an inserted coding region for a heterologous protein of interest, and the RB60 coding region. The final construct described herein for use in a prokaryotic expression system makes a single mRNA from which both proteins are translated. In this embodiment, a separate construct encoding recombinant RB47 as described in Example 4B is co-transformed into the *E. coli* host cell for expression.

The plasmid referred to as pD1/RB60 is prepared as described above for pD1/RB47 in Example 4A with the exception that XhoI and XbaI sites are created on RB60 rather than RB47.

Expression of pD1/RB60 in *E. coli* to produce recombinant RB60 and the recombinant heterologous protein is performed as described in above with the combined expression of RB47 from a separate expression cassette. The heterologous protein is then purified as further described.

To produce an expression cassette that allows for insertion of an alternative desired coding sequence, the plasmid pD1/RB60 is digested with NdeI and XhoI resulting in a vector having restriction endonuclease sites for insertion of a desired coding sequence operably linked to a RB47 binding site and RB60 coding sequence on one transcriptional unit.

G. Constructs Containing RB47 Binding Site Nucleotide Sequence and Heterologous Coding Sequences 1) Expression of Recombinant Tetanus Toxin Single Chain Antibody The examples herein describe constructs that are variations of those described above. The constructs described below contain an RB47 binding site sequence and a heterologous coding sequence. The activating protein RB47 was endogenously provided in the chloroplast and or plant cell. In other aspects however as taught by the methods of the present invention, the chloroplast is further transformed with an RB47-expression construct as described above for overexpression of RB47 to enhance translation capacities.

Figure 7:
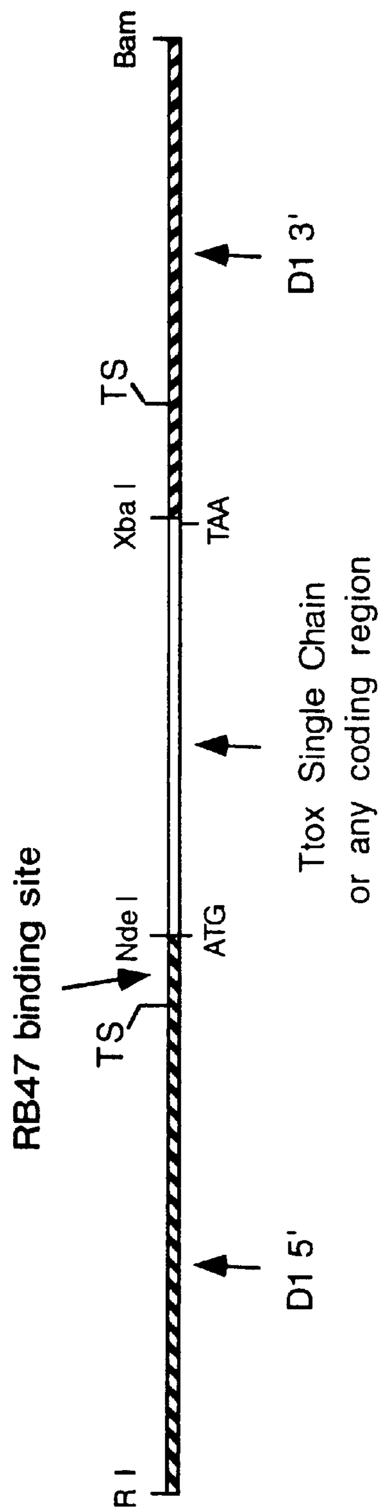

A strain of the green algae *Chlamydomonas reinhardtii* was designed to allow expression of a single chain antibody gene in the chloroplast. The transgenically expressed antibody was produced from a chimeric gene containing the promoter and 5' untranslated region (UTR) of the chloroplast psbA gene prepared as described above, followed by the coding region of a single chain antibody (encoding a tetanus toxin binding antibody), and then the 3' UTR of the psbA gene also prepared as described above to provide for transcription termination and RNA processing signals. This construct is essentially pD1/Nde including a heterologous coding sequence having a 3' XbaI restriction site for ligation with the 3' psbA gene and is diagramed in FIG. 7.

The psbA-single chain construct was first transformed into *C. reinhardtii* chloroplast and transformants were then screened for single chain gene integration. Transformation of chloroplast was performed via bolistic delivery as described in U.S. Pat. Nos. 5,545,818 and 5,553,878, the disclosures of which are hereby incorporated by reference. Transformation is accomplished by homologous recombination via the 5' and 3' UTR of the psbA mRNA.

Figure 8:
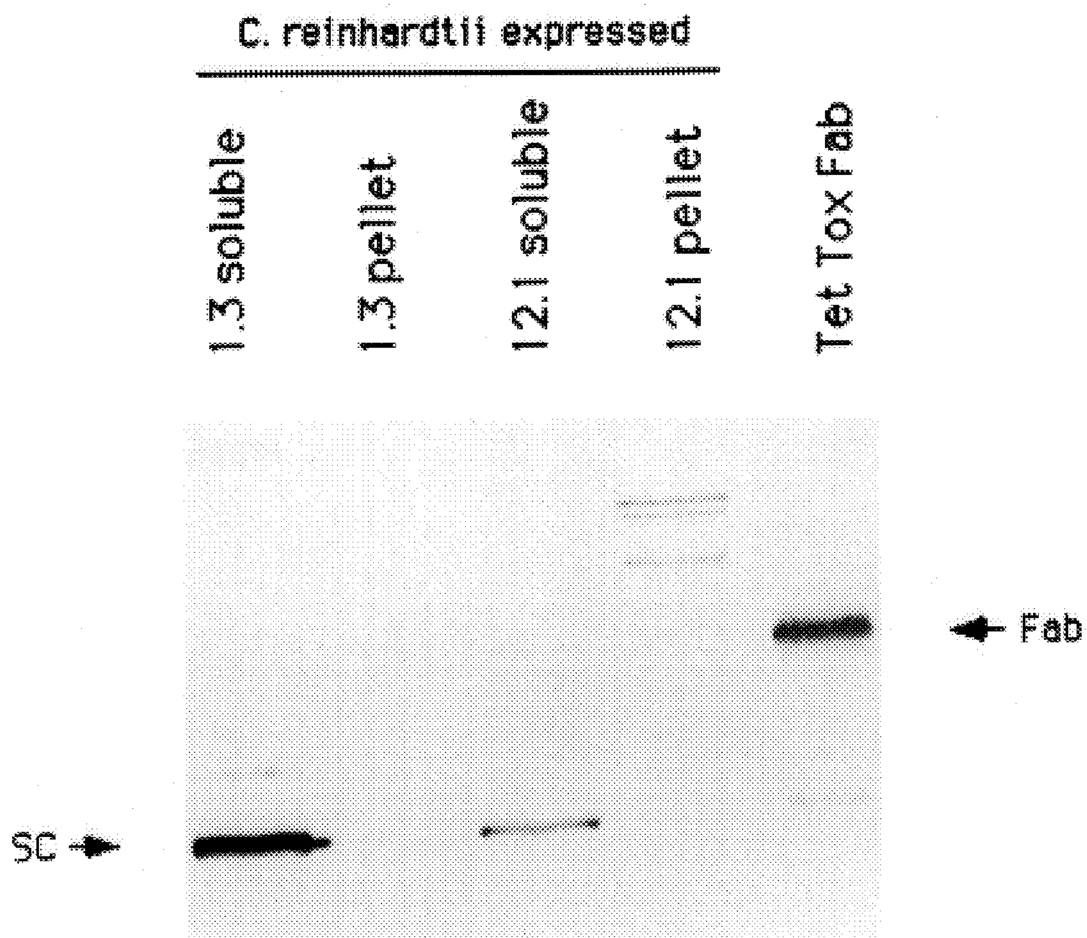

As shown in FIG. 8, two of the transformants that contained the single chain chimeric gene produced single chain antibodies at approximately 1% of total protein levels. The transgenic antibodies were of the correct size and were completely soluble, as would be expected of a correctly folded protein. Few degradation products were detectable by this Western analysis, suggesting that the proteins were fairly stable within the chloroplast. To identify if the produced antibody retained the binding capacity for tetanus toxin, ELISA assays were performed using a mouse-produced Fab, from the original tetanus toxin antibody, as the control. The chloroplast single chain antibody bound tetanus toxin at levels similar to Fab, indicating that the single chain antibody produced in *C. reinhardtii* is a fully functional antibody. These results clearly demonstrate the ability of the chloroplast to synthesis and accumulate function antibody molecules resulting from the translational activation of an RB47 binding site in an expression cassette by endogenous RB47 protein in the chloroplast.

2) Expression of Bacterial Luciferase Enzyme Having Two Subunits

Figure 9:
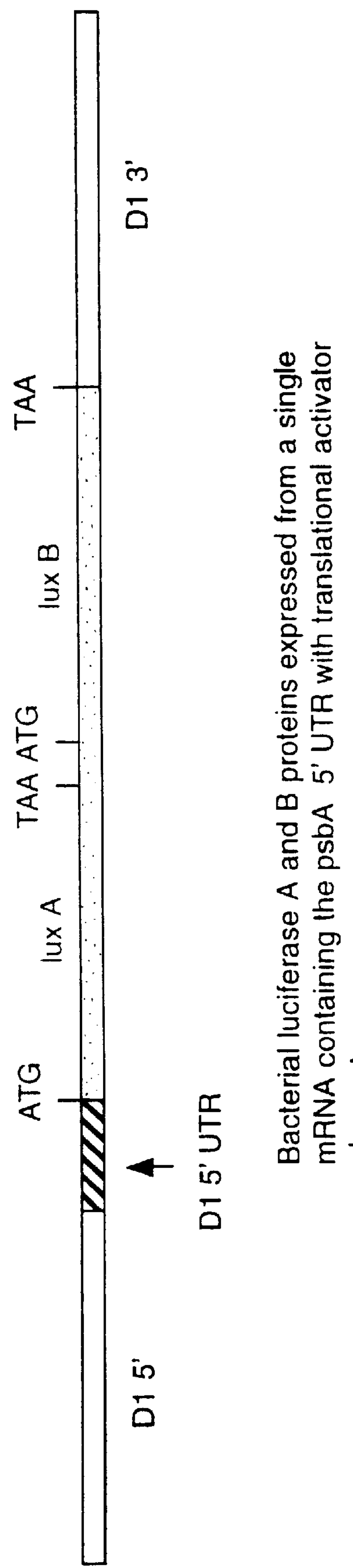
Figure 10:
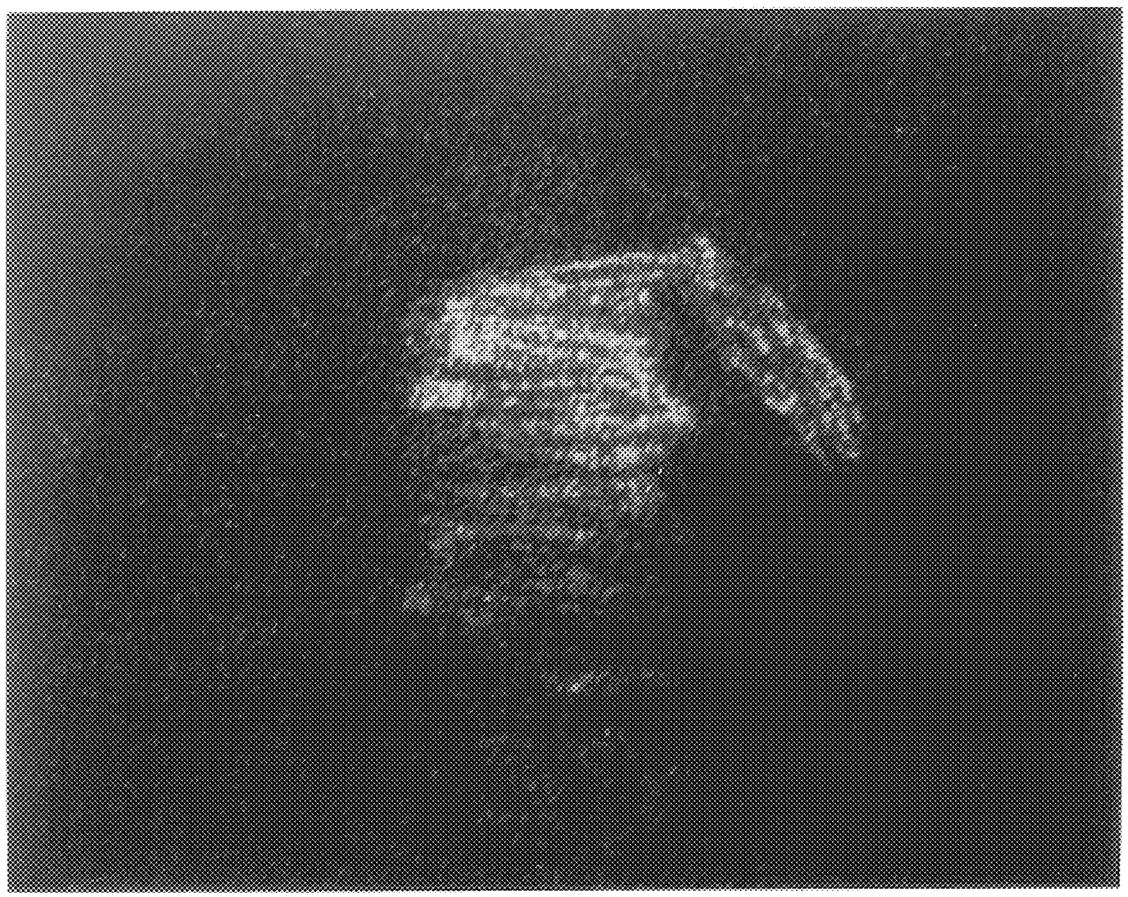

For the production of molecules that contain more than one subunit, such as dIgA and bacterial luciferase enzyme, several proteins must be produced in stoichiometric quantities within the chloroplast. Chloroplast have an advantage for this type of production over cytoplasmic protein synthesis in that translation of multiple proteins can originate from a single mRNA. For example, a dicistronic mRNA having 5' and 3' NdeI and XbaI restriction sites and containing both the A and B chains of the bacterial luciferase enzyme was inserted downstream of the psbA promoter and 5' UTR of the pD1/Nde construct prepared in Example 4A above. In this construct, the bacterial LuxAB coding region was ligated between the psbA 5' UTR and the psbA 3' end in an *E. coli* plasmid that was then transformed into *Chlamydomonas reinhardtii* cells as described above for expression in the chloroplast. A schematic of the construct is shown in FIG. 9. Single transformant colonies were then isolated. A plate containing a single isolate was grown for 10 days on complete media and a drop of the luciferase substrate n-Decyl Aldehyde was placed on the plate and the luciferase visualized by video-photography in a dark chamber. Both proteins were synthesized from this single mRNA and luciferase activity accumulated within the chloroplast as shown in FIG. 10. Some mRNA within plastids contained as many as 5 separate proteins encoded on a single mRNA.

3) Expression of Dimeric IgA

Figure 11:
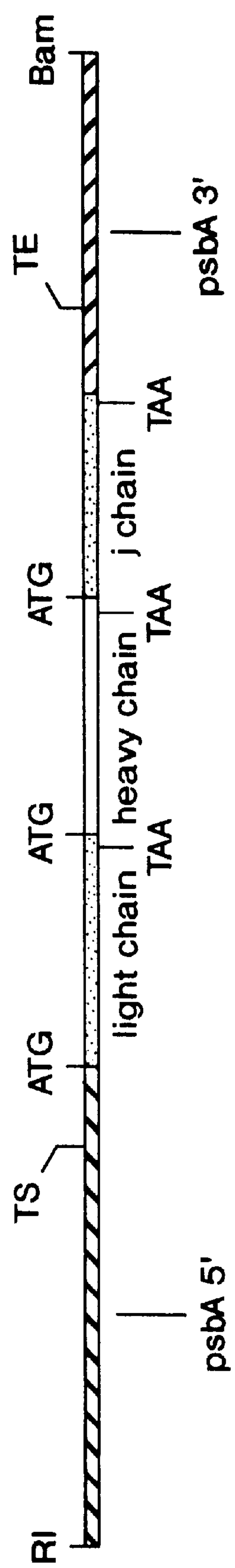

To generate dimeric IgA, the construct shown in FIG. 11 is engineered so that the psbA promoter and 5' UTR are used to drive the synthesis of the light chain and heavy chains of an antibody, and the J chain normally associated with IgA molecules. The nucleic acid sequences for the dimeric IgA are inserted into the RB47 binding site construct prepared in Example 4A. The construct is then transformed into *C. reinhardtii* cells as previously described for expression of the recombinant dIgA.

Production of these three proteins within the plastid allows for the self assembly of a dimeric IgA (dIgA). Production of this complex is monitored in several ways.

First, Southern analysis of transgenic algae is used to identify strains containing the polycistronic chimeric dIgA gene. Strains positive for integration of the dIgA gene are screened by Northern analysis to ensure that the chimeric mRNA is accumulating. Western blot analysis using denaturing gels is used to monitor the accumulation of the individual light, heavy and J chain proteins, and native gels Western blot analysis will be used to monitor the accumulation of the assembled dIgA molecule.

By using a single polycistronic mRNA in the context of RB47 regulated translation, two of the potential pitfalls in the assembly of multimeric dIgA molecule are overcome. First, this construct ensures approximately stoichiometric synthesis of the subunits, as ribosomes reading through the first protein are likely to continue to read through the second and third proteins as well. Second, all of the subunits are synthesized in close physical proximity to each other, which increases the probability of the proteins self assembling into a multimeric molecule. Following the production of a strain producing dIgA molecules, the production of dIgA on an intermediate scale by growing algae in 300 liter fermentors is then performed. Larger production scales are then performed thereafter.

The foregoing specification, including the specific embodiments and examples, is intended to be illustrative of the present invention and is not to be taken as limiting. Numerous other variations and modifications can be effected without departing from the true spirit and scope of the invention.

What is claimed is:

1. An expression cassette for expression of a desired molecule, which cassette comprises:

a) an RB47 binding site nucleotide sequence upstream of a restriction endonuclease site for insertion of a desired coding sequence to be expressed; and b) a nucleotide sequence encoding a polypeptide which binds RB47 binding site.

2. The expression cassette of claim 1 further comprising a promoter sequence operably linked to and positioned upstream of the RB47 binding site nucleotide sequence.

3. The expression cassette of claim 2 wherein the promoter sequence is derived from a psbA gene.

4. The expression cassette of claim 3 wherein the coding sequence is heterologous to the psbA gene.

5. The expression cassette of claim 1 wherein the cassette comprises a plasmid or virus.

6. The expression cassette of claim 1 further comprising and operably linked thereto a nucleotide sequence encoding RB60.

7. The expression cassette of claim 1 wherein the RB47 binding polypeptide is selected from the group consisting of RB47, RB47 precursor and a histidine-modified RB47.

8. An expression cassette for expression of a desired molecule, which cassette comprises:

a) an RB47 binding site nucleotide sequence upstream of a restriction endonuclease site for insertion of a desired coding sequence to be expressed;

and b) a nucleotide sequence encoding a polypeptide which regulates the binding of RB47 to the RB47 binding site.

9. The expression cassette of claim 8 wherein the regulatory polypeptide is RB60.

10. A method of screening for agonists or antagonists of RB47 binding to RB47 binding site, the method comprising the steps:

a) providing a cell expression system containing:
   1) a promoter sequence;
   2) a RB47 binding site sequence;
   3) a coding sequence for an indicator polypeptide; and
   4) a polypeptide which binds to the RB47 binding site sequence;
b) introducing an antagonist or agonist into the cell; and
c) detecting the amount of indicator polypeptide expressed in the cell.

11. A method of screening for agonists or antagonists of RB60 in regulating RB47 binding to RB47 binding site, the method comprising the steps:

a) providing an expression system in a cell containing:
   1) a promoter sequence;
   2) a RB47 binding site sequence;
   3) a coding sequence for an indicator polypeptide;
   4) a polypeptide which binds to the RB47 binding site sequence; and
   5) a RB60 polypeptide;
b) introducing an agonist or antagonist into the cell; and
c) detecting the amount of indicator polypeptide expressed in the cell.

12. An isolated nucleotide sequence encoding RB47.

13. An isolated nucleotide sequence encoding a histidine-modified RB47.

14. An isolated nucleotide sequence encoding RB47 precursor.

15. The nucleotide sequence of claim 12 from nucleotide position 197 to 1402 in FIGS. 1A–1B and SEQ ID NO 5.

16. The nucleotide sequence of claim 13 from nucleotide position 1 to 1269 in FIGS. 5A–5B and SEQ ID NO 14.

17. The nucleotide sequence of claim 14 shown in from nucleotide position 197 to 2065 in FIGS. 1A–1C and SEQ ID NO 5.

18. An expression cassette comprising the nucleotide sequence of claim 12, 13 or 14.

19. An isolated nucleotide sequence encoding RB60.

20. The nucleotide sequence of claim 18 from nucleotide position 16 to 1614 in FIGS. 2A–2B and SEQ ID NO 10.

21. An expression cassette comprising the nucleotide sequence of claim 19.

22. An expression system comprising a cell transformed with the expression cassette of claim 1.

23. The expression system of claim 22 wherein the cell is a plant cell.

24. The expression system of claim 23 wherein the plant cell endogenously expresses RB47.

25. The expression system of claim 23 wherein the plant cell endogenously expresses RB60.

26. The expression system of claim 23 wherein the plant cell endogenously expresses RB47 and RB60.

27. The expression system of claim 22 wherein the cell is a eukaryotic cell.

28. The expression system of claim 22 wherein the cell is a prokaryotic cell.

29. The expression system of claim 22 further comprising the expression cassette of claim 21.

30. An expression system comprising a cell transformed with the expression cassette of claim 8.

31. The expression system of claim 29 further comprising the expression cassette of claim 18.

32. A cell stably transformed with the expression cassette of claim 18.

33. A cell stably transformed with the expression cassette of claim 21.

34. A cell stably transformed with the expression cassette of claims 18 and 21.

35. The expression cassette of claim 1 further comprising an inserted desired coding sequence.

36. An expression system comprising a cell transformed with the expression cassette of claim 35, wherein the coding sequence is expressed forming the desired molecule upon activation of the RB47 binding site with RB47.

37. The expression system of claim 36 wherein the cell is a plant cell endogenously expressing RB47.

38. The expression system of claim 36 wherein the cell is stably transformed with the expression cassette of claim 21.

39. An expression system comprising a cell transformed with an expression cassette comprising a promoter sequence, a RB47 binding site sequence, a desired coding sequence for a molecule, and a nucleotide sequence for encoding a polypeptide which binds RB47 binding site, wherein all sequences are operably linked.

40. A method of preparing a desired recombinant molecule wherein the method comprises cultivating the expression system of claim 36.

41. A method of preparing a desired recombinant molecule wherein the method comprises cultivating the expression system of claim 39.

42. A method for expressing a desired coding sequence comprising:

a) forming an expression cassette by operably linking:
   1) a promoter sequence;
   2) a RB47 binding site sequence;
   3) a desired coding sequence; and
   4) a nucleotide sequence encoding a polypeptide which binds RB47 binding site; and
b) introducing the expression cassette into a cell.

43. The method of claim 42 wherein the cell is a plant cell endogenously expressing RB47.

44. The method of claim 42 wherein the cell is a plant cell endogenously expressing RB60.

45. The method of claim 42 further comprising inducing expression with a promoter inducer molecule.

46. The method of claim 45 wherein the promoter inducer molecule is IPTG.

47. The method of claim 42 wherein the cell is transformed with the expression cassette of claim 21.

48. A method for expressing a desired coding sequence comprising:

a) forming an expression cassette by operably linking:
   1) a promoter sequence;
   2) a RB47 binding site sequence; and
   3) a desired coding sequence;

and b) introducing the expression cassette into a plant cell endogenously expressing RB47.

49. The method of claim 48 wherein the expression cassette further comprises a nucleotide sequence encoding RB60.

50. A method for the regulated production of a recombinant molecule from a desired coding sequence in a cell, wherein the cell contains the expression cassette of claim 34, wherein expression of the coding sequence is activated by RB47 binding to the RB47 binding site thereby producing the recombinant molecule.

51. A method of forming an expression cassette by operably linking:

a) a RB47 binding site sequence;

b) a cloning site for insertion of a desired coding sequence downstream of the RB47 binding site sequence; and c) a nucleotide sequence encoding a polypeptide which binds the RB47 binding site.

52. The method of claim 51 further comprising a promoter sequence operably linked upstream to the RB47 binding site sequence.

53. The method of claim 51 further comprising a desired coding sequence inserted into the insertion site.

54. An article of manufacture comprising a packaging material and contained therein in a separate container the expression cassette of claim 1, wherein the expression cassette is useful for expression of a desired coding sequence, and wherein the packaging material comprises a label which indicates that the expression cassette can be used for expressing a desired coding sequence when the RB47 binding site is activated by RB47.

55. The article of manufacture of claim 54 further comprising in a separate container the expression cassette of claim 18.

56. The article of manufacture of claim 54 further comprising in a separate container the expression cassette of claim 21.

57. An article of manufacture comprising a packaging material and contained therein in a separate container the expression system of claim 22, wherein the expression system is useful for expression of a desired coding sequence, and wherein the packaging material comprises a label which indicates that the expression system can be used for expressing a desired coding sequence when the RB47 binding site is activated by RB47.

58. An article of manufacture comprising a packaging material and contained therein in a separate container the stably transformed cell of claim 32, wherein the cell is useful as an expression system, and wherein the packaging material comprises a label which indicates that the expression system can be used for expressing a desired coding sequence when the RB47 binding site is activated by RB47.

59. An article of manufacture comprising a packaging material and contained therein in a separate container the stably transformed cell of claim 33, wherein the cell is useful as an expression system, and wherein the packaging material comprises a label which indicates that the expression system can be used for expressing a desired coding sequence when the RB47 binding site is activated by RB47 and regulated by RB60.

60. An article of manufacture comprising a packaging material and contained therein in a separate container the stably transformed cell of claim 34, wherein the cell is useful as an expression system, and wherein the packaging material comprises a label which indicates that the expression system can be used for expressing a desired coding sequence when the RB47 binding site is activated by RB47 and regulated by RB60.

61. An article of manufacture comprising a packaging material and contained therein in a separate container the expression cassette of claim 2, wherein the expression cassette is useful for expression of a RNA transcript, and wherein the packaging material comprises a label which indicates that the expression cassette can be used for producing in vitro a RNA transcript when the RB47 binding site is activated by RB47.

62. The article of manufacture of claim 61 wherein the promoter sequence is selected from the group consisting of T3 and T7 promoters.

63. The article of manufacture of claim 61 further comprising in separate containers a polymerase, a buffer and each of four ribonucleotides, reagents for in vitro RNA transcription.

* * * * *